US010040820B2

(12) United States Patent
Colaco et al.

(10) Patent No.: US 10,040,820 B2
(45) Date of Patent: *Aug. 7, 2018

(54) METHOD FOR THE PURIFICATION OF PROTEIN COMPLEXES

(75) Inventors: Camilo Colaco, Cambridge (GB); Colin Richard Bignell, Cambridge (GB)

(73) Assignee: Immunobiology Limited, Cambridge (GB)

( * ) Notice: Subject to any disclaimer, the term of this patent is extended or adjusted under 35 U.S.C. 154(b) by 57 days.

This patent is subject to a terminal disclaimer.

(21) Appl. No.: 13/378,808

(22) PCT Filed: Jun. 21, 2010

(86) PCT No.: PCT/GB2010/051023
§ 371 (c)(1),
(2), (4) Date: Jan. 10, 2012

(87) PCT Pub. No.: WO2010/146401
PCT Pub. Date: Dec. 23, 2010

(65) Prior Publication Data
US 2012/0135029 A1    May 31, 2012

(30) Foreign Application Priority Data

Jun. 19, 2009  (GB) .................... 0910591.7

(51) Int. Cl.
| C07K 1/18 | (2006.01) |
| A61K 39/00 | (2006.01) |
| A61K 39/04 | (2006.01) |
| A61K 39/09 | (2006.01) |
| A61K 39/095 | (2006.01) |
| A61K 39/12 | (2006.01) |
| A61K 39/145 | (2006.01) |
| A61K 39/29 | (2006.01) |
| A61K 39/385 | (2006.01) |
| A61K 39/39 | (2006.01) |
| C07K 14/195 | (2006.01) |

(52) U.S. Cl.
CPC ............ *C07K 1/18* (2013.01); *A61K 39/0011* (2013.01); *A61K 39/04* (2013.01); *A61K 39/092* (2013.01); *A61K 39/095* (2013.01); *A61K 39/12* (2013.01); *A61K 39/145* (2013.01); *A61K 39/29* (2013.01); *A61K 39/385* (2013.01); *A61K 39/39* (2013.01); *C07K 14/195* (2013.01); *A61K 2039/55516* (2013.01); *A61K 2039/605* (2013.01); *C12N 2710/14043* (2013.01); *C12N 2760/16134* (2013.01); *C12N 2770/24234* (2013.01); *Y02A 50/394* (2018.01); *Y02A 50/397* (2018.01); *Y02A 50/403* (2018.01); *Y02A 50/464* (2018.01); *Y02A 50/466* (2018.01); *Y02A 50/478* (2018.01)

(58) Field of Classification Search
None
See application file for complete search history.

(56) References Cited

U.S. PATENT DOCUMENTS

| 5,750,119 A | 5/1998 | Srivastava |
| 5,837,251 A | 11/1998 | Srivastava |
| 5,935,576 A | 8/1999 | Srivastava |
| 5,961,979 A | 10/1999 | Srivastava |
| 5,997,873 A | 12/1999 | Srivastava |
| 6,017,540 A | 1/2000 | Srivastava et al. |
| 6,030,618 A | 2/2000 | Srivastava |
| 6,048,530 A | 4/2000 | Srivastava |
| 6,875,849 B2 | 4/2005 | Graner et al. |
| 7,494,785 B1 | 2/2009 | Shannon et al. |
| 2003/0031661 A1 | 2/2003 | Graner et al. |

FOREIGN PATENT DOCUMENTS

| EP | 1 531 160 | * 12/2003 |
| WO | WO-00/10597 A1 | 3/2000 |
| WO | WO-01/13943 A2 | 3/2001 |
| WO | WO-01/13944 A2 | 3/2001 |
| WO | WO-01/14411 A1 | 3/2001 |
| WO | WO-02/20045 A2 | 3/2002 |
| WO | WO-02/28407 A1 | 4/2002 |
| WO | WO-02/34205 A2 | 5/2002 |
| WO | WO-03/092624 A2 | 11/2003 |
| WO | WO-2010/026432 A1 | 3/2010 |

OTHER PUBLICATIONS

Li et al. Methods 32 (2004) 25-28.*
Reid et al. Cell Stress and Chaperones (1996) 1(2), 127-137.*
Itoh et al., "Mammalian 60-kDa Stress Protein (Chaperonin Homolog)", J Biol Chem: vol. 270, No. 22 1995,13429-13435.
Srivastava, Pramod et al., "Methods of Purification of Heat Shock Protein-Peptide Complexes for Use as Vaccines Against Cancers and Infectious Diseases", Methods in Molecular Biology, 2001, vol. 156, 175-186.
Palleros, Daniel R. et al., "hsp70-Protein Complexes Complex Stability and Conformation of Bound Substrate Protein", vol. 269, No. 18, May 6, 1994, 13107-13114.

(Continued)

*Primary Examiner* — Oluwatosin A Ogunbiyi
(74) *Attorney, Agent, or Firm* — Winstead PC

(57) ABSTRACT

The present invention provides an improved method for the purification of a mixture of complexes comprising a stress protein complexed to a peptide or peptide fragment from a source mixture, typically a cell lysate. The method of the invention provides for protein complexes to be purified using ion exchange chromatography based methods, wherein a modified buffer solution is used which results in the purified stress protein complexes being more immunogenic than protein complexes obtained using conventional methodology. The purified complexes can be used to produce improved vaccine preparations which elicit enhanced immune responses in the subjects to whom the vaccine compositions are administered.

12 Claims, 9 Drawing Sheets

(56) References Cited

OTHER PUBLICATIONS

Reid, Katherine L. et al., "Physical interactions between members of the DnaK chaperone machinery: characterization of the DnaK. GrpE complex", Cell Stress & Chaperones, 1996, 1(2), 127-137.
Menoret, Antoine et al. "Purification of multiple heat shock proteins from a single tumor sample", Journal of Immunological Methods 237, 2000, 119-130.
Palleros, Daniel R. et al., "Interaction of hsp70 with unfolded proteins: Effects of temperature and nucleotides on the kinetics of binding", Proc. Natl. Acad. Sci, USA, Jul. 1991, vol. 88, 5719-5723.
Szabo, Alexander et al., "The ATP hydrolysis-dependent reaction cycle of the *Escherichia coli* Hsp70 system-DnaK, DnaJ, and GrpE", Proc.Natl. Acad. Sci. USA, Oct. 1994, vol. 91, 10345-10349.
Merlos, Ana Maria, "International Search Report", for PCT/GB2010/051023, dated Nov. 30, 2010, 5 pages.
Peng, P., et al., "Purification of immunogenic heat shock protein 70-peptide complexes by ADP-affinity chromatography", Journal of Immunological Methods, Elsevier Science Publishers B.V., Amsterdam, vol. 204, Jan. 1, 1997, pp. 13-21.
Li, Zihai, "In vitro reconstitution of heat shock protein-peptide complexes for generating peptide-specific vaccines against cancers and infectious diseases", Methods: A Companion to Methods in Enzymology, Academic Press Inc., New York, NY, vol. 32, No. 1, Jan. 1, 2004, pp. 25-28.
Chen, Dai-Xiong, et al., "Purification of heat shock protein 70-associated tumor peptides and its antitumor immunity to hepatoma in mice", World Journal of Gastroenterology, Feb. 2004, vol. 10, No. 3, pp. 361-365.
Graner, Michael, et al., "Tumor-derived multiple chaperone enrichment by free-solution isoelectric focusing yields potent antitumor vaccines", Cancer Immunology and Immunotherapy, Springer-Verlag, Berlin, DE, vol. 49, No. 9, Nov. 1, 2000, pp. 476-484.
Kimber, S.J., et al., "A new vaccine approach for Neisseria meningitidis serogroup B using heat shock protein complexes (HspC)", Immunology, Blackwell Publishing, Oxford, GB, vol. 125, No. Suppl. 1, Nov. 21, 2008, p. 126.
Colaco, C.A.L.S., et al., "BCG (Bacille Calmette-Guerin) HspCs (heat-shock protein-peptide complexes) induce T-helper 1 responses and protect against live challenge in a murine aerosol challenge model of pulmonary tuberculosis", Biochemical Society Transactions, Portland Press Ltd, GB, vol. 32, No. 4, Aug. 1, 2004, pp. 626-628.
Palleros, et al., "DnaK, hsp73, and Their Molten Globules. Two Different Ways Heat Shock Proteins Respond to Heat", J Biol Chem (1992) vol. 267, No. 8, pp. 5279-5285.
Palleros, et al., "DnaK ATPase activity revisited", FEBS Letters, Dec. 1993, vol. 336, No. 1, pp. 124-128.
Bleifuss, Elke, et al., "Differential capacity of chaperone-rich lysates in cross-presenting human endogenous and exogenous melanoma differentiation antigens", Int. J. Hyperthermia, Dec. 2008; 24(8); pp. 623-637.
Floto, R. Andres, et al.; "Dendritic Cell Stimulation by Mycobacterial Hsp70 is Mediated through CCR5"; Science, vol. 314; Oct. 20, 2006; pp. 454-458.
Heike, Michael, et al.; "Stress Protein/Peptide Complexes derived from Autologous Tumor Tissue as Tumor Vaccines"; Biochemical Pharmacology, vol. 58; Nov. 1999; pp. 1381-1387.
Cell Signaling Technology Inc, published on 2003 at PhosphoSitePlus, pp. 1-3, 1-4, and 1-5.
Handbooks from Amersham Pharmacia Biotech, "Affinity Chromatography—Principles and Methods", 2001, 156 pages.
Handbooks from Amersham Pharmacia Biotech, "Ion Exchange Chromatography—Principles and Methods", 1999, 157 pages.

* cited by examiner

A

SDS-PAGE analysi  Western Blot analysis

B

A

B

METHOD FOR THE PURIFICATION OF PROTEIN COMPLEXES

FIELD OF THE INVENTION

The present invention relates to a novel methodology for the purification of protein complexes. In particular, there is provided a method for the purification of protein complexes comprising heat shock proteins coupled to peptide fragments. The invention further extends to the use of the purified protein complexes in the preparation of vaccine compositions and in the use of the same for the prevention and treatment of infectious diseases and cancer.

BACKGROUND OF THE INVENTION

Vaccination is widely accepted as the favoured approach to tackle the global healthcare burden of infectious disease and cancer. However, despite significant advances in our understanding of the molecular biology relating to infectious disease and cancers, the development of effective vaccines in these areas has been limited. The most effective vaccines developed use live, attenuated organisms, however, the safety risk associated with such attenuated pathogens reverting to virulence has restricted their widespread use. A further major barrier preventing the wide scale development and use of more effective vaccines is the limited ability to identify candidate pathogen derived proteins that will elicit broad protective immunity in a specific manner against variant strains of microbial pathogens.

One particular approach that shows the promise of conferring broad, protective immunity is the use of stress protein complexes as vaccines against infectious disease and cancer (Colaco et al., (2004) Biochem Soc Trans 32:626-628 and Zeng et al., (2006) Cancer Immunol Immunother 55:329-338). It has also been widely documented that heat shock protein/antigenic peptide complexes are efficacious as vaccines against specific cancers (U.S. Pat. No. 5,997,873; U.S. Pat. No. 5,935,576, U.S. Pat. No. 5,750,119, U.S. Pat. No. 5,961,979 and U.S. Pat. No. 5,837,251). It has been shown that pathogen derived stress protein complexes isolated from heat-shocked BCG cells induced T-helper 1 (Th1) lymphocyte mediated immune responses in a vaccinated host, which conferred protective immunity against a live challenge in a murine aerosol challenge model of pulmonary tuberculosis (International PCT Patent Application No. WO 01/13944). Moreover, it has been shown in WO 02/20045, WO 00/10597 and WO 01/13943 that stress protein complexes isolated from pathogens or pathogen infected cells are effective as the immunogenic determinant within vaccines against infectious diseases.

Heat shock proteins (hsps, HSPs) form a family of highly conserved proteins that are widely distributed throughout the plant and animal kingdoms. On the basis of their molecular weight, the major heat shock proteins are grouped into six different families: small (hsp20-30 kDa); hsp40; hsp60; hsp70; hsp90; and hsp100. Although heat shock proteins were originally identified in cells subjected to heat stress, they have been found to be associated with many other forms of stress, such as infection, osmotic stress, cytokine stress and the like. Accordingly, heat shock proteins are also commonly referred to as stress proteins (SPs) on the basis that their expression is not solely caused by a heat stress. Members of the hsp60 family include the major chaperone GroEL. These form multimeric complexes with co-chaperones such as GroES. Many microbial pathogens have additional hsp60 families that form distinct complexes from GroEL and some hsp60 family members may be more immunogenic, such as the hsp65 of *mycobacteria*. Members of the hsp70 family include DnaK which can form multimeric complexes with co-chaperones such as DnaJ. Other major hsps include the AAA ATPases, the Clp proteins, Trigger factor, Hip, HtpG, NAC, Clp, GrpE, SecB and prefoldin.

Stress proteins are ubiquitously expressed in both prokaryotic and eukaryotic cells, where they function as chaperones in the folding and unfolding of polypeptides. A further role of stress proteins is to chaperone peptides from one cellular compartment to another and, in the case of diseased cells, stress proteins are also known to chaperone viral or tumour-associated peptides to the cell-surface.

The chaperone function of stress proteins is accomplished through the formation of complexes between stress proteins and the chaperoned polypeptide. Chaperoned polypeptides may include peptide fragments, with the formation of such complexes controlled by an ATP-dependent nucleotide exchange system, which has been most clearly demonstrated for the bacterial Hsp70 homologue, DnaK (Szabo et al. PNAS (1994) Vol 91. 10345-10349). Briefly, in its resting cellular state, DnaK is bound to ATP (adenosine triphosphate) and has a low affinity for substrate (Palleros et al. PNAS (1991) Vol. 88. 5719-5723). ATP hydrolysis results in conversion of DnaK to a high-affinity ADP (adenosine diphosphate) state, resulting in the formation of DnaK-ADP-substrate complexes, where the substrate is typically a polypeptide or protein. Following ADP dissociation, ATP re-binds to DnaK, resulting in a conformational change that triggers the release of the correctly folded substrate protein from the complex (Palleros et al J Biol Chem (1992) Vol 267, No 8, 5279-5285; Palleros et al. Nature (1993) 365 (6447):664-6; Szabo et al. PNAS (1994) Vol 91. 10345-10349). This final step, resulting in release of substrate, has been shown to require potassium ($K^+$) and magnesium ($Mg^{2+}$) in addition to the binding of ATP (Palleros et al. Nature (1993) 365(6447):664-6; Palleros et al. FEBS Letters (1993) Vol 336, No 1, 124-128).

Heterologous polypeptides or polypeptide fragments complexed with the stress proteins form stress protein-peptide complexes, which may be referred to as heat shock protein complexes (HspCs). HspCs are captured by antigen presenting cells (APCs) to provide a source of antigenic peptides which can be loaded onto major histocompatibility complex (MHC) molecules for cell surface presentation to the T lymphocytes of the immune system.

Heat shock protein/antigenic peptide fragment complexes (HspCs) have been widely studied as cancer vaccines (see, for example U.S. Pat. No. 5,997,873 and U.S. Pat. No. 5,935,576) and methods have thus been developed for the isolation of HspCs from tumour cells for use as effective vaccines against such tumours. For example, WO 02/28407 discloses a method for use in purifying protein complexes based on the binding affinity of heat shock proteins for heparin. The two step approach involves heparin affinity chromatography and a subsequent ion exchange chromatography step which is optional in order to obtain the stress protein complex preparations. WO 02/34205 relates to the purification of HSP70 stress protein complexes using Con A Sepharose. These methods however result in the isolation of individual families of heat shock proteins, and therefore neglect the use of multiple chaperone proteins as vaccines.

The use of HspCs as cancer vaccines can be significantly improved by the use of multiple chaperone proteins, in particular heat shock proteins (Bleifuss et al 2008) and thus methods have been developed for the purification of multiple chaperone proteins and chaperone protein complexes for use in vaccines. For example U.S. Pat. No. 6,875,849 discloses the use of free-solution isoelectric focusing (FS-IEF) for the purification of HspCs from tumours for use as cancer vaccines. Free flow isoelectric focusing (FF-IEF) can be used to isolate heat shock protein/peptide complexes from pathogens and infected cells for use as the immunogenic determinant in vaccine compositions for the prevention and treatment of infectious diseases. However, a key limitation of that technique has been the difficulties associated with developing a large scale FF-IEF instrument to produce the quantities of heat shock protein/peptide complexes (HspCs) which would be required for large, commercial scale, GMP vaccine manufacture. Moreover, the use of ampholytes (ampholines) to produce the pH gradient required during the FF-IEF process results in the introduction of a further contaminant, in addition to the chaotropes, in the resulting, purified HspC containing preparations. Such contaminants, being unacceptable to Regulatory Authorities, pose a significant barrier to the use of FF-IEF methodology in the manufacture of HspC containing vaccine compositions. Interestingly, these inventors report the stability of HspCs even in the presence use of the chaotropes, such as urea and detergents used during FF-IEF purification even in the absence of divalent cations and ADP in the process buffers (Bleifuss et al 2008). Additionally, the process of free-flow isoelectric focussing is slow with a typical run time of 4 hours, during which high levels of protein degradation result, severely limiting the use of FF-IEF in large scale production of purified protein complexes.

SUMMARY OF THE INVENTION

Following extensive experimentation, the present inventors have identified an improved method for the purification of stress protein-peptide complexes, such as heat shock protein/peptide complexes (HspCs), that can be used to purify multiple stress protein-peptide complexes which can safely be used for vaccine manufacture. This methodology separates the protein complexes on the basis of surface charge rather than isoelectric point. In particular, a purification method has been identified which allows for the rapid purification of a protein complex comprising a stress protein, such as a heat shock protein, complexed to a peptide fragment, wherein the yield of purified product is sufficient to allow the preparation of a commercially acceptable amount of the protein complexes for use in the preparation of a vaccine composition. Advantageously, the purified protein complexes can be used in the preparation of a vaccine preparation due to the absence of pharmaceutically unacceptable or undesirable additives or components introduced during the purification process. Specifically, the inventors have identified the requirement for specific buffer conditions which prevent the breakdown, or partial dissociation on the stress protein complexes. The purification method therefore advantageously reduces or ameliorates dissociation and loss of function of the purified protein complexes when used in a vaccine composition to elicit an immune response thereagainst, whilst concomitantly removing the need to use chaotropes or other chemicals such as surfactants to increase the solubility of the protein complexes undergoing purification. Most surprisingly, the heat shock protein/antigenic peptide complex (HspC) enriched preparations (HEPs) purified using the methodology of the invention elicited significantly enhanced immunity in a vaccinated subject, when compared to the immunity elicited against similar complexes isolated using standard methodology which did not use the buffer conditions of the present invention. The inventors have further identified that the utility of the purified protein complexes of the invention for use in the preparation of a vaccine preparation can be further enhanced when the cell lysate is buffered in a buffer containing adenosine diphosphate (ADP) and at least one divalent cation, or in certain embodiments using only at least one divalent cation. Furthermore, the heat shock protein/antigenic peptide complex (HspC) enriched preparations (HEPs) purified using the improved method of this invention in conjunction with a buffer comprising at least one divalent cation and optionally adenosine diphosphate (ADP) elicited an even greater protective immune responses in subjects to whom the complexes were administered.

According to a first aspect of the present invention there is provided a method for the purification from a source mixture of stress protein complexes formed between a stress protein and a polypeptide, the method comprising the steps of:

(i) providing a source mixture comprising at least one target stress protein complex comprising a stress protein complexed to a polypeptide, (ii) determining the isoelectric point (pI) of at least one target stress protein complex which is to be purified from the source mixture;

(iii) preparing a clarified cell lysate from the source mixture comprising the identified target stress protein complex;

(iv) subjecting the cell lysate to purification using ion exchange, wherein the cell lysate is buffered, using a primary buffer comprising at least one divalent cation, to a pH within 2 units of the pI of the target stress protein complex, and wherein a secondary buffer provides a salt gradient which is used to elute a mixture comprising target stress protein complexes.

In certain embodiments, the primary buffer further comprises adenosine diphosphate (ADP) and/or an adenosine diphosphate mimetic. In certain further embodiments the at least one divalent cation is a magnesium salt, typically magnesium chloride ($MgCl_2$), or a manganese salt. In yet further embodiments the divalent cation is provided at a concentration of from about 0.1 mM to about 100 mM. In one embodiment, the buffer comprises only magnesium salt as the divalent cation, typically magnesium chloride ($MgCl_2$). In certain embodiments the adenosine diphosphate is provided at a concentration of from about 0.1 mM to 100 mM.

In certain embodiments, the primary buffer comprises magnesium chloride ($MgCl_2$) at a concentration of at least 1 mM and adenosine diphosphate (ADP) at a concentration of at least 1 mM. In certain embodiments the buffer further comprises HEPES (4-(2-hydroxyethyl)-1-piperazineethanesulfonic acid), which may be present at a concentration of around 50 mM. Said buffer may have a pH of around pH 6.8.

In certain further embodiments, the primary buffer comprises at least one divalent cation, but lacks at least one of adenosine diphosphate (ADP), adenosine triphosphate (ATP), ATPase and/or potassium or a potassium salt. In one embodiment, the buffer comprises only magnesium salt as the divalent cation, typically magnesium chloride ($MgCl_2$).

In certain further embodiments, the primary buffer lacks at least one of: a chaotrope, a surfactant and/or an ampholyte. Chaotropes (also known as chaotropic agents, or chaotropic reagents) include urea, guanidine hydrochloride and lithium percolate. Chaotropes are known to act as protein denaturants, causing a protein to unfold and a resultant change in three dimensional structure. Ampholytes are molecules which contain both acidic and basic groups. They exist mostly as zwitterions (a chemical compound which has a net charge of zero) in a certain range of pH. Surfactants may include anionic surfactants, such as SDS, cationic surfactants, such as CTAC, HTAB and DTAB, non-ionic surfactants, such as Tween 20, and zwitterionic surfactants, such as DAPS. In certain embodiments, the primary buffer further lacks at least one of: adenosine triphosphate (ATP), ATPase, potassium, or a potassium salt.

In certain embodiments, the mixture of target stress protein complexes which are eluted are provided in a preparation which comprises a plurality of stress proteins of different heat shock protein classes.

Accordingly, advantageously the methodology of the present invention provides a mixture of purified stress protein complexes wherein this mixture of stress proteins comprises different stress protein complexes. That is, the stress protein components of the stress protein complex are a mixture derived from a plurality (i.e. more than one) heat shock protein class or family, for example, there may be a mixture of heat shock proteins derived from the classes HSP60, HSP70 and/or HSP90, or from any other heat shock protein class which is present in a eukaryotic cell, or a pathogenic cell. Specifically any stress protein complex which is present in the cell lysate of a pathogen cell, or a cell infected with a pathogen can be purified by the method of the present invention and therefore present in the final purified product. This mixture of different heat shock proteins is significant as the subsequent administration of the purified complexes as the immunogenic determinant in a vaccine composition results in an enhanced immune response being elicited against the vaccine composition by the immunised host. This enhanced immune response confers improved long term protective immunity against the pathogen against which the subject is being immunised.

Accordingly, in certain aspects, the invention extends to a method of purifying and/or isolating multiple stress protein complexes from a cell lysate obtained from a pathogenic cell, a cell infected with a pathogen, or a tumour cell. Typically the stress protein complexes comprise stress proteins of different stress protein classes. Said purified and/or isolated stress protein complexes, or a preparation or mixture comprising the same, can then typically be used as the immunogenic determinant in a vaccine composition to elicit an immune response and associated protective immunity against the pathogen or tumour cell from which the lysate is derived, or against a pathogen which is infecting a cell from which the lysate is derived. Accordingly, such method would comprise the steps of:

(i) providing a clarified cell lysate from the source mixture comprising the identified target stress protein complex;
(ii) subjecting the cell lysate to purification using ion exchange, wherein the cell lysate is buffered, using a buffer comprising at least one divalent cation, to a pH within 2 units of the pI of the target stress protein complex, and wherein a salt gradient is used to elute the target stress protein complexes, and
(iii) obtaining an enriched preparation comprising a plurality of stress protein complexes.

In certain embodiments, the purifying and/or isolating multiple stress protein complexes or a preparation or mixture comprising the same, comprise stress proteins derived from different families of stress proteins, thus the purified product contains a mixture of stress protein complexes wherein the stress proteins can be derived from different stress protein families, for example, the purified mixture may comprise a plurality of different heat shock protein types which form complexes with peptides.

In certain further aspects, the invention extends to the use of a purified fraction or mixture obtained from a purification methodology, typically ion exchange purification, in particular ion exchange chromatography which is performed according to a method of the present invention, or which purification methodology uses a buffer solution according to the present invention, as the immunogenic determinant in a vaccine composition to prepare a vaccine composition.

Buffer Solutions

In certain further aspects, the invention extends to a buffer solution for use in performing a protein purification method, in particular ion exchange, such as ion exchange chromatography, wherein the purification methodology is based upon the purification, isolation and/or separation of a proteinaceous mixture derived from a cell or cell culture in order to isolate and/or purify a plurality of stress protein complexes therefrom, where the buffer solution comprises at least one divalent cation. In certain embodiments the at least one divalent cation is a magnesium salt, typically magnesium chloride. Further suitable divalent cations are disclosed herein. In certain embodiments, the buffer further comprises adenosine diphosphate (ADP). In certain embodiments, the buffer lacks at least one of, or all of: adenosine triphosphate (ATP), ATPase, potassium, or a potassium salt, chaotropes, ampholytes and surfactants.

Vaccine Compositions

In various further aspects, the invention extends to vaccine compositions, or to compositions which mediate or elicit and immune response, which comprise the purified HspC-enriched lysates or purified and/or isolated multiple stress protein complexes or a preparation or mixture comprising the same, which are obtained by the methods of the invention. Said vaccine compositions are typically administered to mammals, in particular humans in order to confer protective immunity against a pathogen. However, due to the acknowledged high level of homology between stress proteins from different species, vaccine compositions may be used to vaccinate a wide variety of animals.

As such, a further aspect of the invention provides a vaccine composition comprising, as the immunogenic determinant, a purified HspC-enriched eluate fraction or lysate obtained by the present invention. In a preferred embodiment, the invention provides a vaccine composition comprising a purified stress protein-polypeptide complex (HspC)-enriched eluate fraction or lysate, which is obtained by the purification method of the present invention, wherein the lysate is buffered in a buffer comprising at least one divalent cation. The buffer may further comprise adenosine diphosphate. In certain embodiments, the buffer lacks ATP and/or potassium.

A yet further aspect provides a vaccine composition for use in eliciting an immune response in a subject, wherein the immunogenic determinant is purified and/or isolated multiple stress protein complexes or a preparation or mixture comprising the same, obtained using the purification method of the present invention. Specifically, the purification method of the invention comprises isoelectric chromatography which uses the buffer solution described herein to improve the stability and therefore the antigenicity of the stress protein complexes purified from a source proteinaceous mixture.

In certain embodiments, the purified multiple stress protein complexes may be isolated, such that the vaccine composition comprises, as the immunogenic determinant, purified and isolated complexes as the immunogenic determinant of the vaccine composition.

In certain further aspects the present invention provides the use of a vaccine composition according to the invention, or of a purified and/or isolated mixture of stress protein/peptide complexes obtained using the methodology of the invention, for use in medicine.

In certain further aspects the present invention provides for the use of the purified mixture of stress protein-peptide complexes or of a preparation comprising the same, in the preparation of a medicament for the treatment of an infectious disease or a cancerous or a malignant condition.

In certain further aspects, the present invention provides a plurality of stress protein-peptide complexes or of a preparation or mixture comprising the same, which is purified by the method of the first aspect of the present invention for use in a vaccine composition for the treatment or prevention of an infectious disease or a cancerous or a malignant condition.

In certain embodiments, the purified and isolated stress protein complexes or the vaccine compositions containing the same are administered as a prophylactic vaccine. In certain further embodiments, the purified stress protein complexes, preparations comprising the same, or the vaccine compositions containing the same are administered as a therapeutic vaccine.

In various further aspects, the present invention extends to the use of the purified and isolated stress protein complexes, or to preparations or mixtures comprising the same, or to vaccine compositions containing the same, as a booster vaccine to enhance the immune response generated in a host against a pathogen or cancer antigen to which the subject has previously been exposed to, typically by way of infection or due to the previous administration of a primary vaccine.

Compositions of the invention may be lyophilised or in aqueous form, i.e. solutions or suspensions. Liquid formulations of this type allow the compositions to be administered direct from their packaged form, without the need for reconstitution in an aqueous medium, and are thus ideal for injection. Compositions may be presented in vials, or they may be presented in ready filled syringes. The syringes may be supplied with or without needles. A syringe will include a single dose of the composition, whereas a vial may include a single dose or multiple doses (e.g. 2 doses).

In certain embodiments, a vaccine composition according to the invention is formulated for in vivo administration to a subject, such that they confer an antibody titre superior to the criterion for seroprotection for each antigenic component for an acceptable percentage of human subjects. This is an important test in the assessment of a vaccine's efficacy throughout the population. Antigens with an associated antibody titre above which a host is considered to be seroconverted against the antigen are well known, and such titres are published by organisations such as WHO. In one embodiment, more than 80% of a statistically significant sample of subjects is seroconverted, in another embodiment more than 90% of a statistically significant sample of subjects is seroconverted, in a further embodiment more than 93% of a statistically significant sample of subjects is seroconverted and in yet another embodiment 96-100% of a statistically significant sample of subjects is seroconverted. The amount of antigen in each vaccine dose is selected as an amount which induces an immunoprotective response without significant, adverse side effects in typical vaccines. Such amount will vary depending on which specific immunogens are employed. In certain embodiments, the vaccine composition may also elicit a Th1 lymphocyte cell mediated immune response. Such an immune response is desirable when protecting a subject against an intracellular pathogen. In certain embodiments, vaccine compositions comprising the purified stress protein complexes of the invention elicit an immune response in a host which comprises both a cell mediated and humoral (antibody mediated) immune response.

In various further aspects, the present invention provides a method for producing a vaccine composition comprising the step of mixing the purified stress protein complexes or a preparation or mixture comprising the same, of the invention together with at least one pharmaceutically acceptable excipient, carrier or diluent. In one embodiment of the present invention there is provided a vaccine composition for use in a medicament for the treatment or prevention of a pathogenic disease, such as that caused by infection by a pathogenic bacteria selected from the group comprising, but not limited to: *Bordetella pertussis, Clostridium tetani, Clostridium difficile, Corynebacterium diphtheriae, Haemophilus influenzae* b, *Mycobacterium tuberculosis* and *leprae, Salmonella typhi, Streptococcus pneumonia Vibrio Cholerae* and *Neisseria meningitides*. In a further embodiment of the present invention there is provided a vaccine composition for use in a medicament for the treatment or prevention of a pathogenic disease, such as that caused by infection by a pathogenic or oncogenic virus selected from the group comprising, but not limited to: Influenza, Hepatitis, Herpes, HIV, HPV, RSV, Polyoma, CMV, EBV, Rotovirus, Norovirus and SARS. In a yet further embodiment of the present invention there is provided a vaccine composition for use in a medicament for the treatment or prevention of cancer and neoplastic disease.

Additionally, a method of immunising a subject, typically a human, against disease caused *Bordetella pertussis, Clostridium tetani, Clostridium difficile, Corynebacterium diphtheriae, Haemophilus influenzae* type b, *Mycobacterium tuberculosis* and *leprae, Salmonella typhi, Vibrio Cholerae, Streptococcus pneumonia, Neisseria meningitidis* and pathogenic and oncogenic viruses, which method comprises administering to the host an immunoprotective dose of the vaccine of the invention is further provided.

The amount of antigen (i.e. the immunogenic determinant) in each vaccine dose is selected as an amount which induces an immunoprotective response in the vaccinated subject without significant adverse side effects. The amount of antigen will vary depending upon which specific immunogen is employed and how it is presented, however, it will be understood that the enhanced immune response mediated against the purified complexes of the invention will mean that an enhanced immune response will be mediated against an amount of complexes purified using the present methodology, when compared to a vaccine composition comprising a similar amount of protein complexes obtained using the purification methods known in the art.

The invention further provides for the use of the purified HspC-enriched lysates, or isolated stress proteins derived therefrom in a method of vaccinating a subject to induce immunity against a pathogen derived infectious disease or cancerous or malignant condition.

Accordingly a yet further aspect of the invention provides for a method of vaccinating a subject against a pathogen derived infectious disease or a cancerous condition, said method comprising the steps of:

provic'ing a vaccine composition comprising, as the immunogenic determinant, a purified stress protein complex enriched preparation obtained according to the method of the present invention, said purified stress protein-enriched preparation being derived from a cancerous cell, a pathogen, or a cell infected with a pathogen against which protective immunity is desired, and comprising different stress protein types as a mixture within the purified preparation, and administering a vaccine composition comprising the stress protein complex-enriched preparation to a subject in a therapeutically effective or prophylactically effective amount sufficient to elicit an immune response in the subject against the stress protein complex-enriched preparation.

As used herein, the term "vaccine composition" means any composition containing an immunogenic determinant which stimulates the immune system in a manner such that it can better respond to subsequent challenges, pathogenic infections or oncogenesis. It will be appreciated that a vaccine usually contains an immunogenic determinant and optionally an adjuvant, the adjuvant serving to non-specifically enhance the immune response to the immunogenic determinant.

In certain embodiments, the subject is an animal, typically a human. The methods of the invention can also be used to purify stress protein complexes for use in a vaccine composition for the treatment of other animals such as horses, cattle, goats, sheep, swine and birds.

In certain embodiments, the microbial pathogen from which the purified stress protein complexes (HspC-enriched preparations) of the invention are derived, may be selected on the grounds that it causes disease or infection. The vaccine compositions provided by the invention may be used either prophylactically or therapeutically. The inventors however recognise that the compositions may be particularly useful as prophylactic vaccines due to their economy of production and their ability to elicit a protective immune response against the pathogen from which the peptide, or the peptide and stress protein is derived.

The inventors have further surprisingly identified that stress protein-peptide complexes which are obtained using the methods of the invention can be used as "booster" vaccinations, said booster vaccinations enhancing the immunity provided in a subject against a pathogen or a cancerous condition, wherein the initial immunity was conferred by vaccination with a live or attenuated vaccine, or by a vaccine composition wherein the immunogenic determinant was a stress protein-peptide complex.

Accordingly, a yet further aspect of the invention provides for a method of boosting a protective immune response in a subject against a pathogen derived infectious disease or a cancerous condition, wherein said protective immune response has been elicited by the previous administration of a live or attenuated vaccine or of a stress protein-peptide complex comprising a peptide derived from the pathogen against which immunity is desired, said method comprising the steps of:

providing a composition comprising a stress protein/peptide complex-enriched preparation obtained according to the method of the present invention, said purified stress protein/peptide complex-enriched preparation being derived from a cancerous cell, a pathogen infected cell or a pathogen against which protective immunity is desired and comprising different stress protein types as a mixture within the purified preparation, and administering a composition comprising the stress protein/peptide complex-enriched preparation to a subject in an amount sufficient to elicit an immune response in the subject against the stress protein/peptide complex-enriched preparation.

In certain further embodiments, the stress protein/peptide complex containing vaccines of the present invention may be used for the boosting of immune responses in animals that have been previously immunised with other subunit, multi-subunit, carbohydrate or conjugate vaccines. In yet further embodiments, the stress protein/peptide complex vaccines of the present invention can be used to boost the immune responses against a target antigen in animals that have been previously immunised with nucleic acid or live vaccines. In yet further embodiments, the stress protein/peptide complex containing vaccine compositions of the present invention provide for the boosting of immune responses mediated in subjects that have been previously immunised against a pathogen or cancer specific antigen.

In certain further aspects, the present invention extends to vaccine compositions comprising the stress protein-peptide complexes purified by the invention for use in the boosting of immune responses in animals, wherein the animal has previously been vaccinated with a vaccine composition comprising at least one pathogen derived antigen, a pathogen, in particular an attenuated pathogen, or a cancer specific antigen. Typically the peptide component is derived from the same pathogen or cancerous cell, as that which provided the immunogenic determinant for the initial vaccination.

In certain yet further aspects, the present invention extends to vaccine compositions comprising the stress protein-peptide complexes purified by the invention for use in the boosting of immune responses in animals, wherein the animal has previously been exposed to a pathogen or cancer expressing antigens that are present in the stress protein complexes.

In certain further embodiments, the present invention provides compositions for the preparation of cellular vaccines such as dendritic cells (DCs) which have been pulsed with the purified stress protein/peptide complex-enriched preparations of the invention. Administration of such pulsed dendritic cells to subject will result in a T-cell mediated response being directed against the stress protein/antigenic cell complex. Such a therapy can be particularly effective when treating a subject with a cancerous or malignant condition. In such embodiments, typically the stress protein/peptide complex is derived from a cancerous cell.

In certain embodiments, the vaccine composition of the invention may be replaced with a composition for inducing an immune response, or by a composition for eliciting an immune response, said compositions typically comprising the same immunogenic determinants as those provide in the vaccine compositions described herein.

BRIEF DESCRIPTION OF THE FIGURES

FIG. 6A shows the cell mediated immunity induced by HEP vaccines isolated from BCG bacterial cell lysates either in the absence (IEC (2 vaccs) or presence of ADP+a divalent cation (IEC (2vaccs)+ADP/Mg$^{2+}$) compared to vaccination with live BCG (BCG Wk 8) and BCG primed with a HspC boost (BCG/IEC). FIG. 6B shows the Th1 biased humoral immunity induced by HEP vaccines isolated from BCG bacterial cell lysates either in the presence of ADP and a divalent cation (V1), ATP and a divalent cation (V2) or divalent cation alone (V3) and significant enhancement of the antibody response to the current live BCG vaccine (BCG) by boosting with the HspC vaccine (BCG and V1).

DETAILED DESCRIPTION OF THE INVENTION

Figure 1:
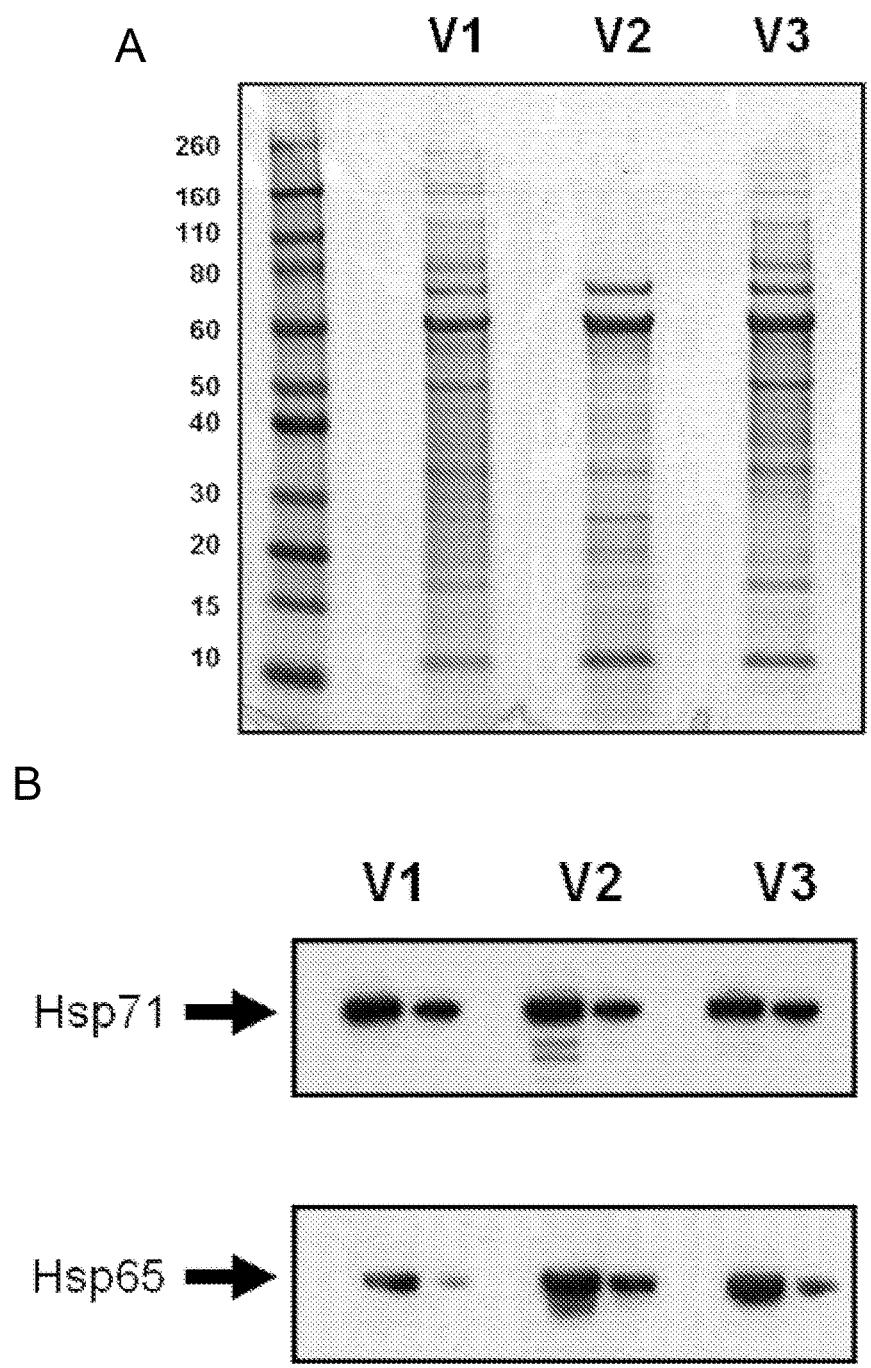
FIG. 1 shows the SDS-PAGE analysis of the purification of protein complexes from BCG bacterial cell lysates (A) and the analysis of these samples for the Hsp71 and Hsp65 proteins by Western blotting (B). V1 is the parent high speed spin lysate from BCG which was processed further to yield V2, HspCs purified using conventional isoelectric focussing methods, and V3, HEPs purified using the first method of this invention.

The present invention provides an improved method for the purification of a mixture of complexes comprising a stress protein complexed to a peptide or peptide fragment from a source mixture, typically a cell lysate. The improved method of the invention provides for protein complexes to be purified using ion exchange based methods, without the need to use chemicals such as chaotropes, surfactants and ampholytes (ampholines) in the purification methodology. Such a method is advantageous as the presence of extraneous ingredients in pharmaceutical preparations is generally undesirable because it causes instability and dissociation of the stress protein/peptide complexes which can result in the stress protein complexes being less immunogenic. Hence, the purified complexes obtained using the method of the invention can be used to produce improved vaccine preparations which elicit enhanced immune responses in the subjects to whom the vaccine compositions are administered. Furthermore, ATP is known to cause the dissociation of stress protein/peptide complexes. However, in the absence of ATP, HspCs are generally regarded to be very stable even when chaotropic agents such as detergents and 7M Urea are used in their purifications. The inventors have surprisingly identified the requirement for stabilisation of the stress protein complexes during purification to yield HspCs that are more immunogenic than similar complexes obtained using purification techniques such as traditional isoelectric focusing (IEF). The inventors have provided an improved ion exchange chromatography methodology which not only prevents the dissociation of the stress protein complexes, due to the presence of at least one divalent cation in the buffer, such as a magnesium salt, but also optionally adenosine diphosphate, which is present in the buffer at a concentration which minimises the dissociation of stress protein complexes. The presence of stable stress protein complexes, as well as the provision of a mixture of stress proteins of different types provides a mixture which can be used as the immunogenic determinant in a vaccine composition and which will elicit an enhanced immune response, over that elicited by a stress protein complex purified using methods which are known in the art.

The method of the invention is further advantageous in that it provides a purification method which has a greater capacity than previous used protein purification techniques, such as isoelectric focusing, for the purification of stress protein complexes, such that the large scale, commercially viable, cost effective production of vaccines containing such complexes can be achieved.

Furthermore, the inventors have surprisingly identified that stress protein complexes which are purified using the methods of the invention are more immunogenic than similar complexes obtained using purification techniques such as traditional isoelectric focusing (IEF). The improved method of the invention provides for protein complexes to be purified using specific buffer compositions and conditions that yield HEPs that show enhanced immunity. Hence, the HspC complexes obtained by the methods of the invention are more immunogenic than those purified using standard purification methods known in the art and can be used to produce improved vaccine preparations.

Source Mixture

Typically the stress protein complexes of the invention are purified or isolated from a source mixture. In certain embodiments, the source mixture is a mixture which comprises at least one stress protein/peptide fragment complex (for which purification is desired) and one or more contaminants. Non-limiting examples of contaminants present in the source mixture may include: host cell proteins other than stress proteins or stress protein complexes, host cell metabolites, host cell constitutive proteins, nucleic acids, endotoxins, chemical product related contaminants, lipids, media additives and media derivatives.

In certain embodiments, the source mixture is a proteinaceous mixture, or is derived from a cell lysate, or a cell homogenate. In certain embodiments, the cell lysate or homogenate is derived from a prokaryotic cell, typically a pathogenic prokaryotic cell, wherein said prokaryotic cell may be an intracellular or extracellular pathogenic bacteria. In certain further embodiments, the cell lysate may be derived from a cell infected with a prokaryotic cell. In further embodiments, the cell lysate or homogenate is derived from a eukaryotic cell, such as a eukaryotic cell infected with a pathogen, for example a prokaryotic pathogen. In certain embodiments, the cell lysate or homogenate is derived from a tumour cell, a cancerous cell mass or tissue, or a cell derived from a biopsy. In certain embodiments, the cells are cells derived from cell culture where the cells are transformed or transfected. In certain further embodiments, the cell lysate or homogenate can be obtained directly from a host cell or pathogenic organism, or from a cell infected by a pathogenic organism. The pathogenic organism may be selected from the group consisting of, but not limited to: (i) a virus, for example, influenza, papilloma virus, herpes simplex virus, hepatitis virus (type A, B or C), HIV, measles and the like, (ii) an intracellular protozoa, such as a trypanosome; or (iii) a cell infected with a prokaryote, in particular an intracellular bacteria, such as a bacteria of the species Mycobacteria or Neisseria. Further examples of source mixtures that can be purified using the method of the present invention include harvested cell culture fluid, cell culture supernatant and conditioned cell culture supernatant. Furthermore, the cell lysate can be derived from a tumour cell In embodiments where the source mixture is derived from, or comprised of a cell lysate, the lysate may be obtained by any suitable means known to the person skilled in the art, including, but not limited to: (i) mechanical means, such as sonication, cavitation, freeze-thaw cycles, the use of a cell homogeniser such as a French press, Dounce homogeniser or motor driven glass/TEFLON homogenizer; (ii) cell lysis using a detergent; or (iii) osmotic lysis by bringing the cells into contact with a hypotonic buffer or hypertonic buffer as required. In certain embodiments where cell lysis is used to produce the source mixture, proteinase inhibitors may further be added to the source mixture.

In certain embodiments, where the source mixture is derived from a homogenised cell preparation, such as a cell lysate or a tissue sample, the homogenate may be centrifuged, at least once, for example at 10,000 g for 30 minutes. The supernatant can then be collected and subjected to further centrifugation, or be prepared for purification using the ion exchange based methodology described herein. In certain further embodiments the centrifugation step may be replaced or complimented by a filtration step.

In certain embodiments, the source mixture is a proteinaceous mixture of proteins, typically a solution comprised of a plurality of proteins. In certain further embodiments, the source mixture is a cell lysate derived from cancerous cells, pathogenic organisms, cells infected with pathogenic organisms, or cell cultures comprising pathogenic organisms, or cells infected therewith.

In certain embodiments, the method of the invention may be used to extract, purify and/or obtain a protein complex from a natural or biosynthetic source. In certain further embodiments, the method may be used to purify a synthetic or recombinant stress protein complex from a cell culture or other protein mixture.

In certain embodiments, the purified complex is present within at least one fraction, such as an eluate fraction. Typically the at least one fraction comprises one or more stress protein/peptide complex. Said fraction may be referred to as a purified product or purification product, and may further be called a heat shock protein/antigenic peptide complex (HspC) enriched preparation (HEP).

Without wishing to be bound by theory, the inventors have identified that an enhanced immune response can be elicited in a subject who is administered a vaccine composition which comprises, as the immunogenic determinant, stress protein/antigenic peptide fragment complex(es) which are derived from a cancerous cell, a pathogenic cell, a cell infected by a pathogenic organism, or a prokaryotic or eukaryotic cell which has been genetically modified such that it expresses a heterologous protein which is derived from a cancerous cell or a pathogen which causes an infectious disease in a host, wherein the heterologous protein causes an immune response to be mounted there-against when administered to a subject. As such, in certain embodiments, the purified product typically comprises a mixture of antigenic peptide/heat shock protein complexes.

Stress Protein

In certain embodiments, the stress protein complex can be a heat shock protein complex (HspC) comprising a heat shock protein which is complexed to a peptide fragment.

In certain embodiments, the heat shock protein can be any suitable heat shock protein which is derived from the cell lysate which is to be purified. In certain embodiments, the heat shock protein may be selected from any one of the families of the group comprising, but not limited to: hsp20-30 kD; hsp40; hsp60; hsp70; hsp90; and hsp100. In certain further embodiments, the stress protein may be a protein which is classed as a chaperone protein. Such a protein may include, but is not limited to proteins selected from the group consisting of: DnaK, DnaJ, GroEL, GroES, hspX, acr2, AAA+, clpA/B, HtpG, TRIC, CCT, IbpA, IbpB, calrecticulin, hsp40, hsp70, hsp72, hsp90, grp94, grp75, BiP/grp78, grp75/mt, gp96 and small hsps.

In certain embodiments, the target stress protein complex comprises a heat shock protein/antigenic peptide fragment complex derived from a host cell which has been genetically modified to constitutively express stress protein genes, and/or express a heterologous protein, such as an antigenic peptide or peptide fragment. In certain further embodiments, the cell may be a host cell expressing a heterologous gene, for example an insect cell infected with a baculovirus vector construct comprising an antigenic gene of interest. In yet further embodiments, the cell may be a cancerous cell derived from a human or animal subject.

In certain embodiments, where a mixture of complexes is provided, this may comprise heat shock proteins of one particular family, for example, the hsp70 or hsp60 families, although it is preferred that the mixture comprises different heat shock protein complexes derived from different families. The method of the present invention would provide a method for the purification of all complexes comprising a heat shock protein complexed to an (antigenic) peptide fragment, irrespective of the identity, molecular weight or size of the antigenic peptide or peptide fragment.

In certain further embodiments, the heat shock protein/antigenic peptide complex (HspC) enriched preparations (HEP) comprise heat shock proteins from different stress protein families or classes, such as hsp60, hsp65, hsp70 and hsp90, said families being co-purified as a mixture using the methods of the invention.

In certain further embodiments, the heat shock protein/antigenic peptide complex (HspC) enriched preparations (HEP) may be heat shock protein/peptide fragment complexes of a particular molecular weight. In certain embodiments, the stress protein complexes have a molecular weight in the range of 50 KDa to 900 KDa.

Antigenic Peptide Fragment

In certain embodiments, the polypeptide which is conjoined to the stress protein to for the stress protein complex (HspC) is a peptide fragment, that is, the peptide fragment is a fragment of a larger polypeptide or protein. Typically the peptide is an antigenic peptide, that is, a proinflammatory response would be mediated against the polypeptide in a host to whom the peptide is administered. The peptide or antigenic peptide should be suitable to allow a T cell (cell mediated) or antibody mediated (humoral) immune response to be raised against it in the host to whom the stress protein complex is administered. Typically, the polypeptide is derived from a pathogen, or a cell infected with a pathogenic cell, against which an immune response is desired. In certain further embodiments, the polypeptide is derived from a malignant or cancerous cell, or a cell lysate containing the same, wherein the polypeptide or peptide fragment is a tumour specific antigen.

In certain embodiments, the peptide is complexed to the stress protein in a non-covalent manner. In certain further embodiments, the peptide is complexed to the stress protein by means of a covalent bond.

In certain embodiments, the peptide fragment is an antigenic peptide fragment derived from a pathogenic organism wherein the pathogenic organism typically causes an infectious disease in a host. In certain embodiments, the pathogenic cell may be a prokaryotic cell, such as a gram positive or gram negative bacteria, or an intracellular or extracellular bacterial pathogen. In certain further embodiments, the pathogen is a viral pathogen, or a peptide fragment derived therefrom. In certain further embodiments, the pathogen may be a protozoa, a parasite or a fungi, such as a yeast.

In certain embodiments, the pathogenic cell from which the antigenic peptide is derived may be prokaryote selected from the group consisting of, but not limited to members of the genus *Escherichia, Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma.*

In certain embodiments, the antigenic peptide fragment may be a viral peptide. The virus from which the peptide can be derived may be selected from the group consisting of, but not limited to: human immunodeficiency virus (HIV), hepatitis A virus (HAV), hepatitis B (HBV), hepatitis C(HCV), any other hepatitis-associated virus, human papillomavirus (HPV) especially high-risk oncogenic human papillomavirus types, Kaposi's Sarcoma-Associated Herpesvirus (KSHV) (also known as Human Herpesvirus-8 (HHV-8)), Herpes Simplex virus (HSV) (any subtype), Respiratory Syncytial Virus (RSV) and associated respiratory viruses, Influenza viruses including avian influenza and swine influenza, particularly if these are transmissible to humans, coronaviruses including SARS-associated Coronavirus (SARS-CoV), rhinovirus, adenovirus, SIV, rotavirus, human papilloma virus, arbovirus, measles virus, polio virus, rubella virus, mumps virus, papova virus, cytomegalovirus, varicella-zoster virus, varicella virus, huntavirus and any emergent virus, in particular Ebola virus, Marburg virus, West Nile virus (WNV), St Louis Encephalitis virus (SLEV), Rift Valley Fever virus (RVFV) and other members of the Bunyaviridae.

In certain embodiments where the antigenic peptide fragment is derived from a protozoan pathogen, the protozoa may typically be an intracellular protozoan, such as *leishmania* or *trypanosoma.*

In embodiments where the antigenic peptide fragment is derived from a yeast or fungi, said fungi may be derived from a genus selected from the group comprising: *Acremonium, Alternaria, Amylomyces, Arthoderma, Aspergillus, Aureobasidium, Blastochizomyces, Botrytis, Candida, Cladosporium, Crytococcus, Dictyostelium, Emmonsia, Fusarium, Geomyces, Geotrichum, Microsporum, Neurospora, Paecilomyces, Penicillium, Pilaira, Pityrosporum, Rhizopus, Rhodotorula, Saccharomyces, Stachybotrys, Trichophyton, Trichoporon,* or *Yarrowia.*

In certain embodiments, the antigenic peptide fragment may be derived from a tumour cell. In such embodiments, typically the antigenic peptide fragment is, or is a fragment of, a tumour specific antigen. In certain embodiments the tumour cell may be derived from a cancerous or malignant condition selected from the group including, but not limited to, Acute and Chronic Myelogenous Leukemia (AML, CML), Follicular Non-Hodgkins lymphoma, malignant melanoma, Hairy Cell leukaemia, multiple myeloma, carcinoid tumours with carcinoid syndrome and liver and lymph node metastases, AIDS related Kaposi's sarcoma, renal cell carcinoma, adenocarcinoma of the large bowel, squamous cell carcinoma of the head and neck. Furthermore, it would be well known to the person skilled in the art that some infectious diseases can cause cancer in subjects whom they infect. Accordingly, administration of the complexes purified according to the methodology of this invention wherein the polypeptide is derived from an infectious disease can be used to treat or prevent cancer. For example, a complex comprising a polypeptide derived from human papillomavirus can be used to treat or prevent cervical cancer in a suitable subject.

In certain further embodiments, the antigenic peptide fragment which is complexed to the stress protein is a heterologous protein or peptide fragment which is expressed in a host cell by recombinant means, for example, by introduction into the host cell of a vector or similar construct. In certain embodiments, the heterologous antigen may be derived from a bacterial pathogen, a viral pathogen or is a tumour specific antigen.

In certain further embodiments, the host cell may be a eukaryotic cell which is infected by an intracellular pathogen. In such embodiments, the stress protein complex may comprise a heat shock protein derived from the host cell complexed to an antigenic peptide fragment derived from the intracellular pathogen, or a stress protein and peptide fragment which are both derived from the intracellular pathogen.

In certain embodiments of the invention, the source mixture is a cell lysate which is produced from a cell population which has been exposed to a stress inducing stimuli which is suitable to cause the induced (as opposed to the constitutive) expression of stress proteins, typically heat shock proteins. In certain embodiments, the stress inducing stimuli is selected from the group comprising, but not limited to: heat shock, osmotic shock, pressure and nutrient deprivation. In certain other embodiments, the stress induction is achieved by the genetic modification of a cell to cause the constitutive expression of a heat shock protein gene. In one such embodiment the genetic modification is the inactivation of repressor genes that suppress the expression of stress proteins such as the hspR and HrcA repressor genes in microbial pathogens. Other such genetic modifications are described in WO 2002/020045 and citations referred to therein.

For the non-genetic induction of stress proteins, the optimum conditions for inducing the stress proteins can readily be determined by simple trial and error with the effect of a change of stress stimuli being assessed with regard to levels of stress protein production using conventional techniques, such as those described in Current Protocols in Immunology, Wiley Interscience, 1997. Other such conditions are described in WO 2001/013944 and the citations referred to therein.

In one embodiment, at least one heat shock protein/antigenic peptide complex (HspC) enriched preparations (HEP) which is purified using the methods of the present invention comprise heat shock protein/antigenic peptide fragment complexes (HspCs), which include, but which are not limited to hspC65, hspC70, hspC90 and hspC100.

Ion Exchange Conditions

The method of the invention is based on separating proteins using a methodology based on ion exchange chromatography. However, the presently described method has been improved over standard ion exchange chromatography protocols and procedures currently used in the art, through the removal of chemicals, which are typically present in the buffer solution, which may adversely affect protein structure and integrity, which may cause the dissociation or partial dissociation of protein complexes, or which may result in contaminants being present in the purified fractions. The method therefore employs a modified ion exchange methodology to produce an enriched or purified preparation comprising stress protein complexes, which may also be referred to as an HEP (HspC enriched preparation).

Ion exchange chromatography (IEC) relies on charge-charge interactions between proteins present in the sample mixture (cell lysate) and the charges immobilized on the resin or matrix used. Ion exchange chromatography may take the form of cation exchange chromatography, in which positively charged ions bind to a negatively charged resin, or anion exchange chromatography, in which the protein binding ions have a negative charge, and the immobilized functional matrix or resin has a positive charge. Once the protein present in the sample mixture is bound to the resin, the column is washed to equilibrate this with a starting buffer. Typically this buffer is of low ionic strength. In the methods of the present invention, the inventors employ the use of a buffer which comprises at least one divalent cation, such as magnesium or manganese, which is typically provided in a salt form, such as magnesium chloride. The buffer may further comprise adenosine diphosphate, which is present in the buffer at a level which will significantly inhibit the dissociation of the stress protein/peptide complexes. Such a buffer has been identified by the inventors as protecting the structural stability of the stress protein complexes, as the buffer prevents the dissociation of the stress protein-peptide complexes during the purification process. The method of the present invention provides that the bound stress protein complexes are then eluted off in fractions by changing the salt gradient present in the column, typically through the use of a second buffer solution, such as sodium chloride (NaCl) or a sodium chloride based solution. The eluted fractions are collected, with the fractions eluted at different pIs (isoelectric points) containing different stress protein complexes. As the pI of the desired protein complexes has been identified, the eluted fraction containing the complexes of interest will be readily identifiable. Typically the methodology of the present invention will result in a purified (or isolated) mixture of stress protein complexes. Unlike traditional ion exchange chromatography based purification methods which result in the recovery of stress protein complexes of one family (such as HSP70), the methodology of the present invention provides a purified product (which may also be referred to as an isolated product wherein a mixture of different stress proteins is present. For example, if the cell lysate is derived from a eukaryotic cell infected with a pathogen, then the resulting purified product may comprise stress protein complexes, wherein the stress protein is at least 2 of HSP60 or HSP70. Any other heat shock protein found within the cell lysate may also be present in the purified product. Furthermore, if during the preparation of the cell lysate, the pathogen which is infecting the eukaryotic cell is also lysed, then the methods of the present invention further allow for pathogen derived stress protein/peptide complexes to be present in the purified product. For example, the purified product may comprise a mixture of stress protein complexes where the stress proteins may be selected from the group comprising: HSP40, HSP60, HSP70, HSP84, HSP90, Dna-K and Dna-J.

The isoelectric point (pI) is the pH at which a particular molecule, such as the protein complexes of the invention, has no net electrical charge. The pI value of a protein or protein complex can be determined from its primary sequence, or empirically using conventional isoelectric focussing techniques and commercially available equipment. The pI value of the protein complex can be used to affect the solubility of the protein at a particular pH. Protein molecules contain both acidic and basic functional groups. Further, amino acids may be positive, negative or neutral in charge. These factors give a protein its overall charge. At a pH lower than their pI, proteins carry a net positive charge. At a pH above their pI, proteins carry a net negative charge. Proteins have minimum solubility in salt solutions at the pH which corresponds to their pI. This can lead to the protein complex precipitating out of solution. It is therefore desirable that when varying the salt gradient in accordance with the method of the invention, that the pH is not lowered from the initial pH as this may result in the protein complexes precipitating out of solution. Typically therefore, once the pH is set, it is not increased. In certain embodiments, the increase of the salt gradient results in an increase in pH.

As such, in certain embodiments, the method comprises varying the salt concentration of a buffer solution used in the column matrix, for example by using a buffer solution comprising sodium chloride. Typically this variation in the salt gradient of the buffer causes the stress protein complexes to be eluted, typically in fractions consistent with changes in the salt concentration. Accordingly, in certain embodiments, the progressive addition of the elution buffer provides a salt gradient. Typically, the elution buffer contains sodium chloride (NaCl), and the salt gradient can be varied by varying the presence of sodium chloride (NaCl) in the elution buffer to which the matrix is exposed. In certain embodiments, sodium chloride may be present in the buffer at a concentration of 150 mM, 250 mM, 350 mM, or 500 mM. In certain embodiments, the elution buffer provides a pH gradient which can be varied as the constituents of the buffer are varied. In certain embodiments the elution buffer comprises at least one divalent cation, and optionally adenosine diphosphate.

In certain embodiments, the stress protein complexes are present in fractions collected which are eluted and which have a pI in the range of pI 4 to pI 8. In certain embodiments, the pI of the stress proteins which are to be purified may be firstly determined by isoelectric focussing.

In certain embodiments, the purification methodology is not performed in the presence of (i.e. it is performed in the absence of) urea or a similar compound or solution. In certain other embodiments, ampholytes, chaotropes and/or surfactants are not used in the purification methodology. In certain preferred embodiments the buffer contains at least one divalent cation and may further contain adenosine diphosphate.

Typically the method comprises the steps of (i) applying the source mixture to an ion exchange matrix, (ii) adjusting the pH, varying the salt gradient across the ion exchange matrix, and (iii) collecting the eluted fractions, wherein said fractions comprise purified or enriched stress protein complexes, the elution of which is caused by the changing of the salt gradient under specific conditions. In certain embodiments, the matrix is a resin. In further embodiments, the matrix is a membrane. Typically the matrix is comprised of charged particles.

In certain embodiments, the ion exchange is performed using an ion exchange membrane absorber which serves to separate complex protein mixtures into basic and acidic fractions. The inventors have identified that that form of ion exchange results in a method which is convenient, fast and reproducible and which therefore can produce a consistently high yield of stable stress protein complexes, which have their integrity maintained, as would be required for the production of commercial quantities of a vaccine preparation which comprised a protein component, such as a stress protein-peptide complex as the immunogenic determinant. Furthermore, in certain embodiments where stress protein complexes are for use as the immunogenic determinant in the preparation of vaccine compositions and wherein the stress protein complexes are purified in the presence of a buffer comprising at least one divalent cation, and in certain preferred embodiments adenosine diphosphate, the inventors have identified that such stress protein complexes have superior utility in mediating or enhancing immune responses elicited by the use of such vaccines as the complexes remain in a more stable state, that is, the complexes do not dissociate to become a separate stress protein and peptide fragment. In certain embodiments, the buffer lacks at least one of adenosine triphosphate (ATP), ATPase, potassium, or a potassium salt, chaotropes, ampholytes and surfactants.

In one embodiment, the heat shock protein/antigenic peptide complex (HspC) enriched preparations (HEP) can be eluted from the ion exchange chromatography medium using any suitable elution buffer known to the skilled person in order to maintain protein integrity. Typically the elution buffer comprises a salt, such as sodium chloride, as described hereinbefore. The elution buffer may further comprise a phosphate or TRIS based buffer, acetate, citrate or a hydrogen ion buffer.

The terms "ion-exchange" and "ion-exchange chromatography" as used herein refer to a chromatographic process in which an ionizable solute of interest (e.g., a protein complex of interest provided in a cell lysate) interacts with an oppositely charged ligand linked to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange, anion exchange, and mixed mode chromatographies.

In certain embodiments, the ion exchange chromatography medium includes an ion exchange column. Typically, the ion exchange column includes a high flow base, such as an agarose or sepharose high flow base. Optionally the high flow base includes a surface extender, such as animal free dextran. Suitable ion exchange media include both cation and anion exchange resins and columns including those derivatized with quaternary ammonium salts and sulphonic moieties, for examples the CAPTOQ™ column and CAPTOS™ resins (GE Healthcare Limited). In further embodiments the ion exchange chromatography medium includes a mixed multimodal ion exchange resins, for example the Capto® MMC and CAPTO® Adhere columns (GE Healthcare).

In certain embodiments, the cell lysates are buffer exchanged into 50 mM phosphate buffer pH6.8. In certain embodiments, the ion exchange column includes a high flow base, preferably an agarose high flow base. In certain embodiments, the high flow base includes a surface extender, e.g. animal free dextran, and a Q ligand, e.g. a quaternary ammonium salt.

The phrase "ion exchange material" refers to a solid phase that is negatively charged (i.e. a cation exchange resin) or positively charged (i.e. an anion exchange resin). In one embodiment, the charge can be provided by attaching one or more charged ligands (or adsorbents) to the solid phase, e.g. by covalent linking. Alternatively, or in addition, the charge can be an inherent property of the solid phase (e.g. as is the case for silica, which has an overall negative charge).

In certain embodiments, where the ion exchange chromatography is cation exchange chromatography, the cation exchange chromatography step employs a ligand selected from the group comprising, but not limited to: sulfonate, carboxylic, carboxymethyl sulfonic acid, sulfoisobutyl, sulfoethyl, carboxyl, sulphopropyl, sulphonyl, sulphoxyethyl and orthophosphate.

A "cation exchange resin" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP Sepharose FAST FLOW™, SP Sepharose High Performance from GE Healthcare, Toyopearl SP-650S and SP-650M from Tosoh, Macro-Prep High S from Bio-Rad, Ceramic HyperD S, Trisacryl M and LS SP and Spherodex LS SP from Pall Technologies); a sulfoethyl based group (e.g., Fractogel SE from EMD, or Poros S-10 and S-20 from Applied Biosystems); a sulphopropyl based group (e.g., TSK Gel SP 5PW and SP-5PW-HR from Tosoh, Poros HS-20 and HS 50 from Applied Biosystems); a sulfoisobutyl based group (e.g., Fractogel EMD SO3 from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrex Cellufine C500 and C200 from Millipore, CM52, CM32, CM23 and Express—Ion C from Whatman, Toyopearl CM-650S, CM-650M and CM-650C from Tosoh); sulfonic and carboxylic acid based groups (e.g. BAKERBOND™ Carboxy-Sulfon from J. T. Baker); a carboxylic acid based group (e.g., WP CBX from J.T Baker, DOWEX MAC-3 from Dow Liquid Separations, Amberlite Weak Cation Exchangers, DOWEX™ Weak Cation Exchanger, and Diaion Weak Cation Exchangers from Sigma-Aldrich and Fractogel EMD COO—from EMD); a sulfonic acid based group (e.g., Hydrocell SP from Biochrom Labs Inc., DOWEX™ Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX™ Strong Cation and Diaion Strong Cation Exchanger from Sigma-Aldrich); and a orthophosphate based group (e.g., pI 1 from Whatman).

If desirable, a cation exchange membrane can be used instead of a cation exchange resin, for example, Sartobind S (Sartorius; Edgewood, N.Y.).

In certain embodiments, where the ion exchange chromatography is anion exchange chromatography, the anion exchange chromatography step may employ a ligand selected from the group consisting of: quaternary ammonium or amine, dethylamine, diethylaminopropyl, amino, trimethylammoniumethyl, trimethylbenzyl ammonium, dimethylethanolbenzyl ammonium, polyamine.

An "anion exchange resin" refers to a solid phase which is positively charged, thus having one or more positively charged ligands attached thereto. Any positively charged ligand attached to a solid phase suitable to form the anionic exchange resin can be used, such as quaternary amino groups. For example, a ligand used in AEC can be a quaternary ammonium, such as quaternary alkylamine and quaternary alkylalkanol amine, or amine, diethylamine, diethylaminopropyl, amino, trimethylammoniumethyl, trimethylbenzyl ammonium, dimethylethanolbenzyl ammonium, and polyamine. Alternatively, for AEC, a membrane having a positively charged ligand, such as a ligand described above, can be used instead of an anion exchange resin.

Commercially available anion exchange resins include, but are not limited to, DEAE cellulose, Poros PI 20, PI 50, HQ 10, HQ 20, HQ 50, D 50 from Applied Biosystems, MonoQ, MiniQ, Source 15Q and 30Q, Q, DEAE and ANX Sepharose Fast Flow, Q Sepharose high Performance, QAE SEPHADEX™ and FAST Q SEPHAROSE™ from GE Healthcare, WP PEI, WP DEAM, WP QUAT from J. T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Q HyperZ, Trisacryl M and LS DEAE, Spherodex LS DEAE, QMA Spherosil LS, QMA Spherosil M from Pall Technologies, DOWEX Fine Mesh Strong Base Type I and Type II Anion Resins and DOWEX MONO-SPHER E 77, weak base anion from Dow Liquid Separations, Matrex Cellufine A200, A500, Q500, and Q800 from Millipore, Fractogel EMD TMAE$_3$ Fractogel EMD DEAE and Fractogel EMD DMAE from EMD, Amberlite weak and strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and 650C$_3$ QAE-550C and 650S, DEAE-650M and 650C from Tosoh, and QA52, DE23, DE32, DE51, DE52, DE53, Express-Ion D and Q from Whatman.

If desirable, an anion exchange membrane can be used instead of an anion exchange resin. Commercially available anion exchange membranes include, but are not limited to, SARTOBIND Q™ from Sartorius, MUSTANG Q™ from Pall Technologies and INTERCEPT Q™ membrane from Millipore.

In certain embodiments, the anion exchange chromatography is performed at a pH of from about pH 5.0 to about pH 9.0 and at a conductivity of from about 0.5 to about 5 mS/cm. In certain embodiments, the cation exchange chromatography is performed at a pH of from about pH 4.0 to about pH 9.0 and at a conductivity of from about 0.5 to about 15 mS/cm. In certain embodiments, the mixed mode chromatography is performed at a pH of from about pH 4.0 to about pH 9.0 and at a conductivity of from about 0.5 to about 15 mS/cm.

The "pI" or "isoelectric point" of a polypeptide refers to the pH at which the polypeptide's positive charge balances its negative charge. The pI can be calculated according to various conventional methodologies, e.g., from the net charge of the amino acid and/or sialic acid residues on the polypeptide or determined empirically using isoelectric focusing techniques.

The pH and conductivity of the chromatography buffer are selected such that the HspCs of interest are bound to the IEC resin used. Examples of buffers suitable for use as an elution buffer may include a phosphate or TRIS based buffer, acetate, citrate and the hydrogen ion buffers (Good et al., 1966 *Biochemistry* 5: 467-477).

The term "elution buffer", as used herein, refers to a buffer used to elute the protein complexes of interest from the resin. The pH and conductivity of the elution buffer are selected such that the protein complexes of interest are eluted from the CEC resin used in the process. Examples of buffers suitable for use as an elution buffer may include a phosphate or TRIS based buffer, acetate, citrate, glycine, histine and the Good buffers.

In certain embodiments, the elution buffer is sodium chloride (NaCl) which may be used at a concentration of from about 50 mM to about 1500 mM. In certain further embodiments, the elution buffer comprises at least one divalent cation, and in certain embodiments adenosine diphosphate. In certain embodiments, the buffer lacks at least one of adenosine triphosphate (ATP), ATPase, potassium, or a potassium salt, chaotropes, ampholytes and surfactants.

The pH of the elution buffer can be from about pH 3 to about pH 10, more preferably pH from about pH 4 to about pH 9. In certain embodiments, the pH of the buffer is about pH 6.8.

The present invention further extends to HspC-enriched lysates (HEL) which are purified according to the methods of the present invention. Said HspC-enriched lysates may also be known as an HspC-enriched fraction (HEF) or as HspC enriched compositions (HEC). Accordingly, a further aspect of the present invention provides at least one HspC-enriched lysate purified by the method of invention for use in the preparation of a vaccine composition. Typically the HspC-enriched lysate is derived from at least one eluted fraction obtained from the ion exchange method of the present invention.

In certain embodiments, the HspC-enriched lysate comprises a complex formed between a stress protein (heat shock protein) and a polypeptide or peptide fragment, in particular an antigenic peptide fragment. In certain embodiments, the purified HspC-enriched lysate is derived from a microbial host, prokaryotic, viral or protozoal pathogen, a eukaryotic host cell infected with a pathogen, or from a malignant or cancerous cell. In a preferred embodiment, the purified complex is a stress protein/peptide complex comprises a mixture of stress proteins wherein the stress protein can be selected from the group consisting of small hsps, hsp65, hsp70, hsp90 and hsp100.

Ion Exchange Chromatography (IEC) relies on charge-charge interactions between the proteins in the sample and the charges immobilized on the resin of choice. In general IEC can be subdivided into cation exchange chromatography or anion exchange chromatography. For example CaptoQ™ (a positively charged anion exchanger) may be utilised when the target protein complex is predicted to be negatively charged at pH6.8 (see table 1) and CaptoS™ (a negatively charged anion exchanger) may be utilised when the target protein complex is predicted to be positively charged at pH6.8.

TABLE 1

Predicted binding of Hsps to CaptoQ column

| Protein | MW (kDa) | pI | Predicted binding to CaptoQ* |
|---|---|---|---|
| Hsp90 | 75 | 4.7 | strong |
| Hsp71 | 67 | 4.9 | strong |
| Hsp60 (Cpn60.1/groEL1) | 56 | 4.7 | strong |
| Hsp65 (Cpn60.2/groEL2) | 57 | 4.6 | strong |
| HspX | 16 | 5 | strong |
| BCG-A (GroES) | 11 | 4.6 | strong |

*phosphate buffer pH6.8 used for column equilibration

Moreover, the distribution of the isoelectric point (pI) of proteins in a proteome is universal for all prokaryotes and can be represented as a bimodal distribution or "butterfly effect" such that approximately 60% of the proteins have a pI and 40% of the proteome has a pI≥8 (see Table 1). For example, where stress protein complexes from mycobacterial cultures are used to generate a cell lysate, it would be expected that at pH 6.8 at least 40% of the mycobacterial contaminating proteome would be readily removed from the purified complex and hence also from vaccine product using CaptoQ™ IEC. The skilled man will readily understand that the methods of the present invention may be performed using any suitable ion exchange medium which is a high performance medium.

Important technical issues to consider when developing a robust protein purification strategy include a short process run time and careful consideration of the buffer composition. The present inventors have provided a method for the purification of protein complexes and in doing have overcome issues associated with protein degradation, modification or disruption of the proteins complexes during the purification process. Although immunogenic HspC enriched vaccines have been prepared with free flow isoelectric focusing (FF-IEF), typical run times were 4 hours and it was also necessary to maintain protein solubility with chaotropes such as urea. This chaotrope has been shown to have destabilizing effects on both macromolecular structure and protein function. Encouragingly, CaptoQ™ due to the chemical stability of the high flow 'protein friendly' matrix results in a shorter run time and offers a greater flexibility of buffer choice. The present invention has surprisingly reduced the time taken to prepare 3 mg of HspC (stress protein complex) enriched preparation from 10 mg of starting lysate to approximately 2 hours. Moreover protein solubility was maintained without the need for chaotropes or surfactants. Additionally, protein degradation levels were reduced. The buffer compositions of the present invention minimised the disruption of the protein complexes during the purification process and the HEPs produced by the methods of the present invention showed enhanced immunogenicity and protection against infection. Preferred buffer comprise at least one divalent cation and optionally adenosine diphosphate The methods of the present invention have been used to prepare potential vaccines against tuberculosis (TB), meningitis and influenza and are simple, predictable, and straightforward, with the process performance defined almost exclusively by the isoelectric point of the target proteins and the buffer pH. The vaccine composition may comprise at least 2 two of the major heat shock proteins thought to be important in eliciting protective immunity in a host, specifically Hsp60 or GroEL, and Hsp70 or DnaK families and homologues.

The methods of the present invention have the advantage of being scalable and rapid with the possibility of processing liters of lysate to generate Kg amounts of purified protein complex and vaccine composition.

Administration of Vaccine Compositions

In certain embodiments, the vaccine compositions of the invention may further comprise at least one adjuvant. In certain embodiments, the adjuvant is selected from the group consisting of, but not limited to; Freund's complete adjuvant, Freund's incomplete adjuvant, Quil A, Detox, ISCOMs and squalene. Further suitable adjuvants include mineral gels or an aluminium salt such as aluminium hydroxide or aluminium phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-0-deacylated MPL, quit A, Saponin, QS21, Freund's Incomplete Adjuvant (Difco Laboratories, Detroit, Mich.), Merck Adjuvant 65 (Merck and Company, Inc., USA), AS-2, AS01, AS03, AS04, AS15 (GSK, USA), MF59 (Chiron, Sienna, Italy), CpG oligonucleotides, bioadhesives and mucoadhesives, microparticles, liposomes, outer membrane vesicles, polyoxyethylene ether formulations, polyoxyethylene ester formulations, muramyl peptides or imidazoquinolone compounds.

The vaccine compositions or purified and/or isolated stress protein complexes of the present invention may be administered to a subject in need of treatment via any suitable route. Typically the composition is administered parenterally. Examples of other possible routes for parenteral administration include, but are not limited to; intravenous, intracardial, intraarterial, intraperitoneal, intramuscular, intracavity, subcutaneous, transmucosal, inhalation or transdermal. Routes of administration may further include topical and enteral, for example, mucosal (including pulmonary), oral, nasal, rectal. The formulation may be a liquid, for example, a physiologic salt solution containing non-phosphate buffer at pH 6.8-7.6, or a lyophilised or freeze dried powder.

In certain embodiments, the composition is deliverable as an injectable composition. For intravenous injection, the stress protein complexes will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

In certain embodiments, the injection method can be needless or may use a needle which penetrates the dermis. In certain further embodiments the vaccine is suitable for oral administration, or can be administered transdermally, or by pulmonary delivery. In certain embodiments, the vaccine composition is administered as a prophylactic vaccine. In certain embodiments, the vaccine composition is administered as a therapeutic vaccine. In yet further embodiments the vaccine composition is administered as a booster vaccine to any previously administered vaccine mediated by a primary immunisation schedule.

Pharmaceutical compositions for oral administration may be in tablet, capsule, powder or liquid form. A tablet may comprise a solid carrier such as gelatine or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, N. C. et al. 7th Edition ISBN 0-683305-72-7, the entire disclosures of which is herein incorporated by reference.

The vaccine compositions or purified and/or isolated stress protein complexes of the present invention may also be administered via microspheres, liposomes, other microparticulate delivery systems or sustained release formulations placed in certain tissues including blood.

Dosage regimens can include a single administration of the composition of the invention, or multiple administrative doses of the composition. The compositions can further be administered sequentially or separately with other therapeutics and medicaments which are used for the treatment of the condition for which the composition of the present invention is being administered to treat.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

Definitions

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived.

As used herein, the term "treatment" and associated terms such as "treat" and "treating" mean the eliciting of protective immune response against an immunogenic determinant in order to confer long term protective immunity against the pathogen or cancer cell from which the immunogenic determinant of the vaccine composition is derived. The term 'treatment' therefore refers to any regimen that can benefit a subject. The treatment may be in respect of an existing condition or may be prophylactic (preventative treatment). Treatment may include curative, alleviative or prophylactic effects.

As used herein, the term "therapeutically effective amount" means the amount of a stress protein complex or vaccine composition of the invention which is required to induce a protective immune response against an infectious disease or cancerous condition. As used herein, the term "prophylactically effective amount" relates to the amount of a multiple stress protein complex or vaccine composition which is required to prevent the initial onset, progression or recurrence of an infectious disease or cancerous condition. The term "therapeutic" does not necessarily imply that a subject is treated until total recovery. Similarly, "prophylactic" does not necessarily mean that the subject will not eventually contract a disease condition.

A "subject" in the context of the present invention includes and encompasses mammals such as humans, primates and livestock animals (e.g. sheep, pigs, cattle, horses, donkeys); laboratory test animals such as mice, rabbits, rats and guinea pigs; and companion animals such as dogs and cats. It is preferred for the purposes of the present invention that the mammal is a human. The term "subject" is interchangeable with the term "patient" as used herein.

As used herein, the terms "mount", "mounted", "elicit" or "elicited" when used in relation to an immune response mean an immune response which is raised against the immunogenic determinant of a vaccine composition which is administered to a subject. Typically the immunogenic determinant of the vaccine composition comprises the isolated and/or purified stress protein complexes obtained using the methods of the present invention.

As used herein, the term "immune response" includes T cell mediated and/or B cell mediated immune responses that are influenced by modulation of T cell co-stimulation. The term immune response further includes immune responses that are indirectly effected by T cell activation such as antibody production (humoral responses) and the activation of cytokine responsive cells such as macrophages.

EXAMPLES

The present invention will now be described with reference to the following examples which are provided for the purpose of illustration and are not intended to be construed as being limiting on the present invention.

Example 1: Preparation of HspC-Enriched Preparations from BCG Cellular Lysates

BCG cell pellets from mid-log heat shocked cultures were lysed and clarified by centrifugation. Cell pellets were resuspended in sterile PBS containing an EDTA-free protease inhibitor cocktail. Resuspended cells were lysed using sonication, a Beadbeater or passed through an Emulsiflex C5 high pressure homogeniser and collected in a sterile bag. Benzonase (250 U/mL) was added to the lysate. The samples were then homogenised a further two times, the cellular lysate transferred to centrifuge tubes and cell debris removed by centrifugation for 20 minutes at 6000 g. The clarified lysate was collected and centrifuged for a further 60 minutes at 14000 g and the supernatant was removed and referenced as high speed clarified lysates. 10 ml of clarified lysates were desalted and buffer exchanged into 50 mM phosphate buffer pH 6.8. The protein concentration of the sample was determined and an IEC (ion exchange chromatography) HspC enriched preparation was prepared by column chromatography as follows. 10 mg of protein was loaded on to a CaptoQ™ column at a flow rate of 0.5 ml/minute. After extensive washing of the column with 50 mM phosphate buffer, pH 6.8 proteins were batch eluted using increasing concentrations of NaCl (150 mM, 300 mM, 500 mM and 1M). Eluted fractions containing Hsp70 and Hsp65 were analysed using SDS-PAGE and Western blotting using commercial antisera against DnaK and GroEL. Examples of the HEPs prepared are shown in FIGS. 1A (SDS-PAGE) and 1B (Western blotting). In some preparations, a mixed modal MMC column was used with loading in 50 mM Acetate, 1M NaCl, 1 mM $MgCl_2$ at pH5 and elution in the same buffer at pH 8.0.

Figure 5:
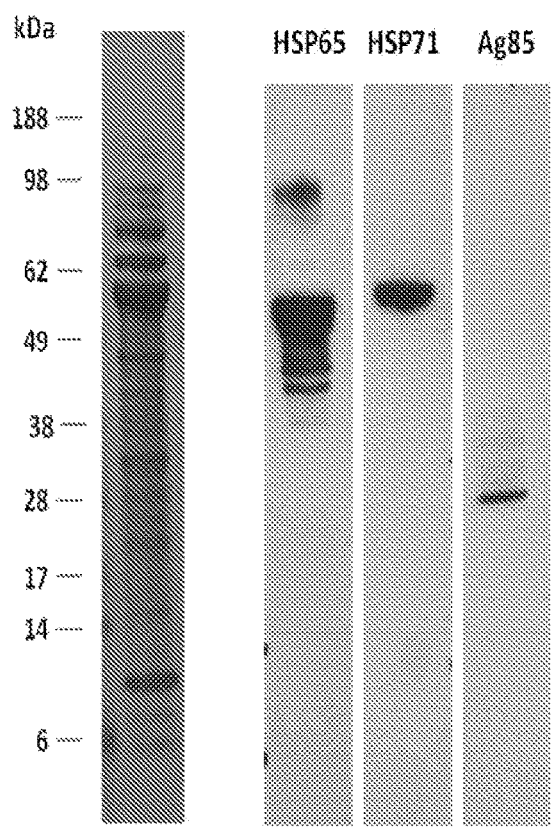
FIG. 5A shows Western blot analysis of HEPs from BCG bacterial cell lysates purified in the presence of ADP+a divalent cation. Lane 1 shows Coomasie blue stained SDS-PAGE, while lanes 2 to 4 show recognition of Hsp65, Hsp71 and Ag85, respectively, by Western blot.
FIG. 5B shows Coomaise blue stained SDS-PAGE of HEPs from BCG bacterial cell lysates purified in the presence of divalent cation (BCG 001/09), plus ADP (HspC Vac) or ATP (BCG 002/09).
Figure 5:
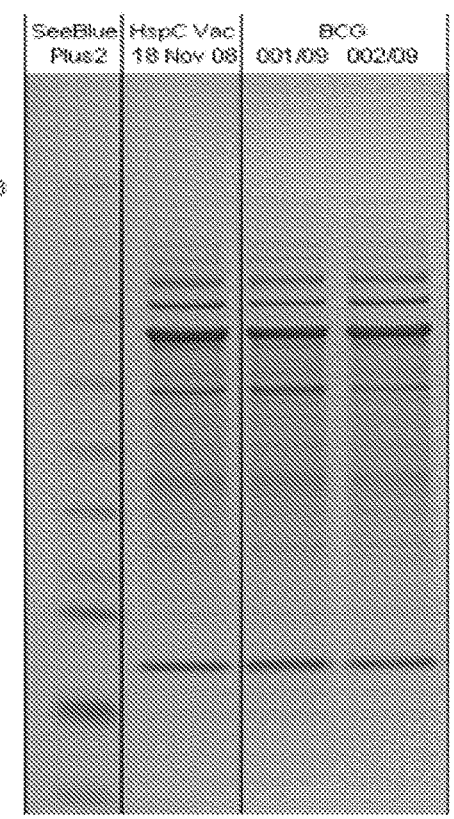

Example 2: Enhancing Complex Stability in the Preparation of HspC-Enriched Preparations from BCG Cellular Lysates BCG cell pellets from mid-log heat shocked cultures were lysed and clarified by centrifugation. Cell pellets were resuspended in sterile PBS containing an EDTA-free protease inhibitor cocktail. Resuspended cells were lysed using sonication, a Beadbeater or passed through a Emulsiflex C5 high pressure homogeniser and collected in a sterile bag. Benzonase (250 U/mL) was added to the lysate. The samples were then homogenised a further two times, the cellular lysate transferred to centrifuge tubes and cell debris removed by centrifugation for 20 minutes at 6000 g. The clarified lysate was collected and centrifuged for a further 60 minutes at 14000 g and the supernatant was removed and referenced as high speed clarified lysates. 10 ml of clarified lysates were desalted and buffer exchanged into 50 mM HEPES, 1 mM $MgCl_2$, pH 6.8 with or without 1 mM ADP. The HspC enriched preparation was isolated using column chromatography on a CaptoQ™ column. After extensive washing of the column with 50 mM HEPES, 1 mM $MgCl_2$, pH 6.8, with or without 1 mM ADP, proteins were batch eluted using increasing concentrations of NaCl (150 mM, 350 mM, 500 mM and 1M). Eluted fractions containing Hsp70 and Hsp65 were analysed using SDS-PAGE and Western blotting using commercial antisera against DnaK (Hsp70), GroEL (Hsp65) and Ag85. Examples of the HEPs prepared are shown in FIG. 5A. Control HEPs containing disrupted HspC complexes were prepared using buffer compositions with ATP replacing ADP (FIG. 5B). Although the HEPs prepared in the various buffers did not show significant differences in their Coomasie Blue stained protein profiles (FIG. 5B), they differed greatly in their immunogenicity as shown in Example 3 below.

Example 3: Immunogenicity of BCG Derived HspC-Enriched Preparations

BCG HEPs were used to immunise BalbC mice and spleens harvested from the immunised animals 28 days after immunisation. Spleens were collected into RPMI-1640 and single cell suspensions were made by pressing the spleens through 70 μm cell strainers using a 5 mL syringe plunger into a 50 mL Falcon tube. Cells were counted using trypan blue exclusion on a KOVA glasstic slide haemocytometer and the production of interferon gamma (IFN-γ) assayed in a recall response to TB antigens.

$2 \times 10^6$ splenocytes were added to each well in a 24 well tissue culture plate (Nunc) in 1 mL culture medium and to each well, one of the following antigens was added: BSA (10 μg/ml), Con A (10 μg/ml), TB whole cell lysate (WCL at 50 to 1.56 μg/mL), HEPs, IEF HspCs or Ag85 (10 μg/mL).

Figure 2:
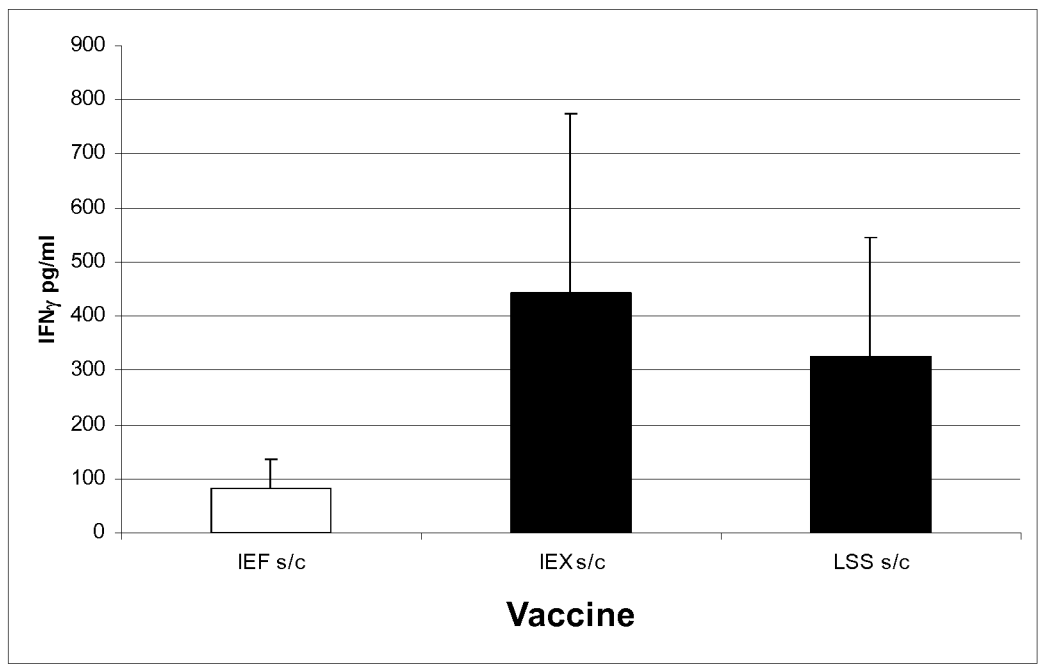
FIG. 2 shows the immunogenicity of the HEPs isolated from BCG (IEX) using the first method of this invention, compared to the parent lysate (LSS) and HspCs isolated using conventional isoelectric focussing methods (IEF).
Figure 6:
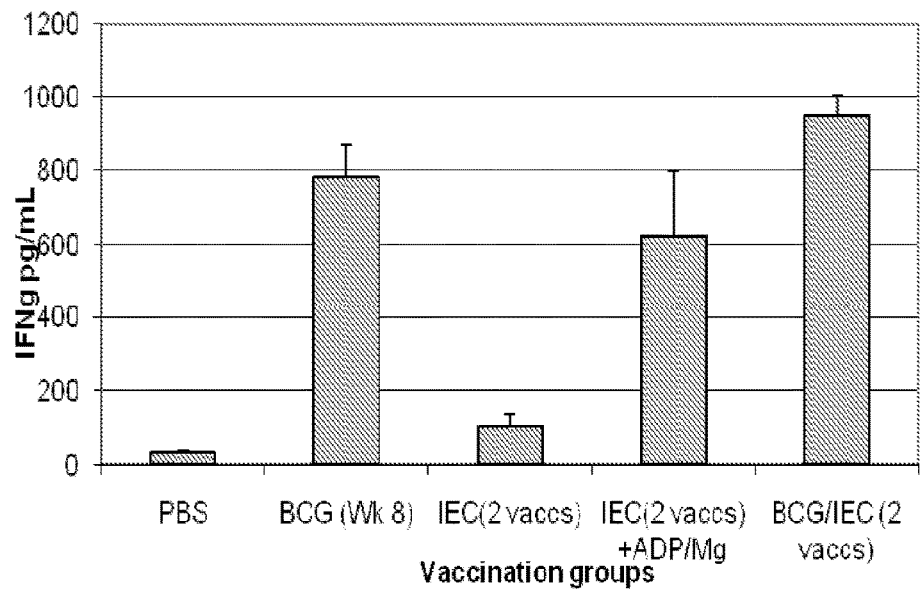
FIG. 6 shows the immunogenicity of the HEPs isolated from BCG.
Figure 6:
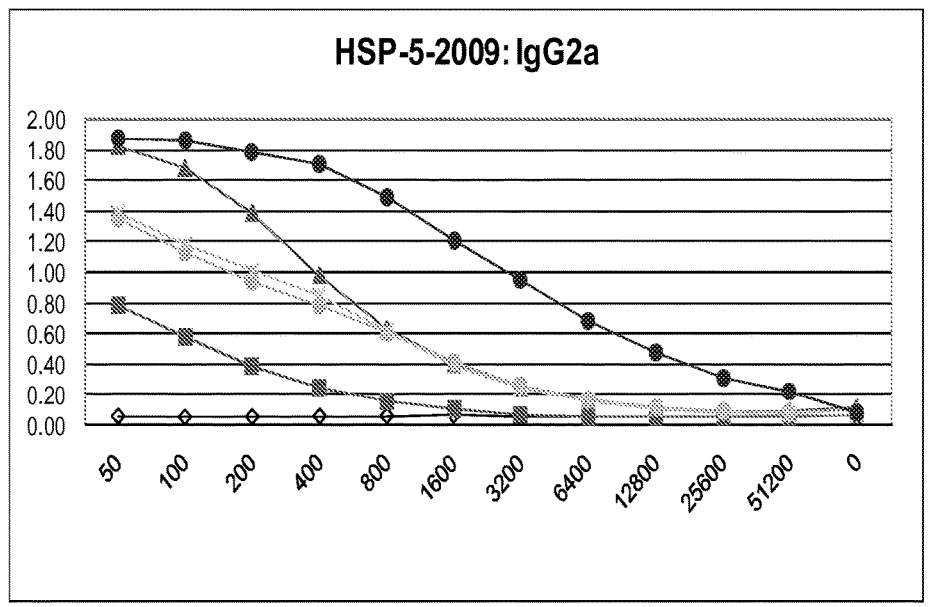

Culture supernatants from the re-stimulated wells were tested for IFN-γ IL-2, IL-4 and IL-5 using a murine ELISA kit according to the manufacturer's protocol (R&D Systems). FIG. 2 shows typical results obtained with spleen cells from immunised mice re-stimulated with WCL in vitro. The results show that HEPs isolated from BCG (IEX) induced a strong IFN-γ response in the immunised animals, stronger than the parent BCG lysates (LSS) and much stronger than HspCs isolated using conventional free-flow isoelectric focussing method previously described (IEF) for the isolation of multiple HspC families. Recall responses to WCL were comparable to those seen with Con A and significant but smaller responses were seen against Ag85. The in vitro IFN-γ responses also translated into in vivo protection against live TB challenge in the mouse aerosol challenge model. FIG. 6 shows the detailed immunogenicity of the HEPs isolated from BCG. FIG. 6A shows typical results for cell mediated immunity obtained assayed using spleen cells from immunised mice re-stimulated with WCL in vitro. The results show that HEPs isolated from BCG as in Example 2, in the presence of ADP and divalent cations (IEC (2 vaccs) and ADP/Mg), induced a strong IFN-γ response in the immunised animals, stronger than the HEPs isolated from BCG as in Example 1 (IEC (2 vaccs), and similar to the response seen in animals immunised with live BCG and boosted with these HEPs (BCG/IEC (2 vaccs)).

FIG. 6B shows the Th1-bias of the humoral immunity induced by HEP vaccines isolated from BCG bacterial cell lysates either in the presence of ADP+a divalent cation (V1), ATP+a divalent cation (V2) or divalent cation alone (V3) and demonstrate the enhanced immunogenicity of HEPs isolated using the improved buffer compositions of the present invention. FIG. 6B also shows the significant enhancement of the Th1 induced IgG2a antibody response to the current live BCG vaccine (BCG) by boosting with the HspC vaccine (BCG+V1) prepared by the improved methods of the present invention.

Example 4: Protective Immunity Induced by BCG HspC Vaccines

Figure 7:
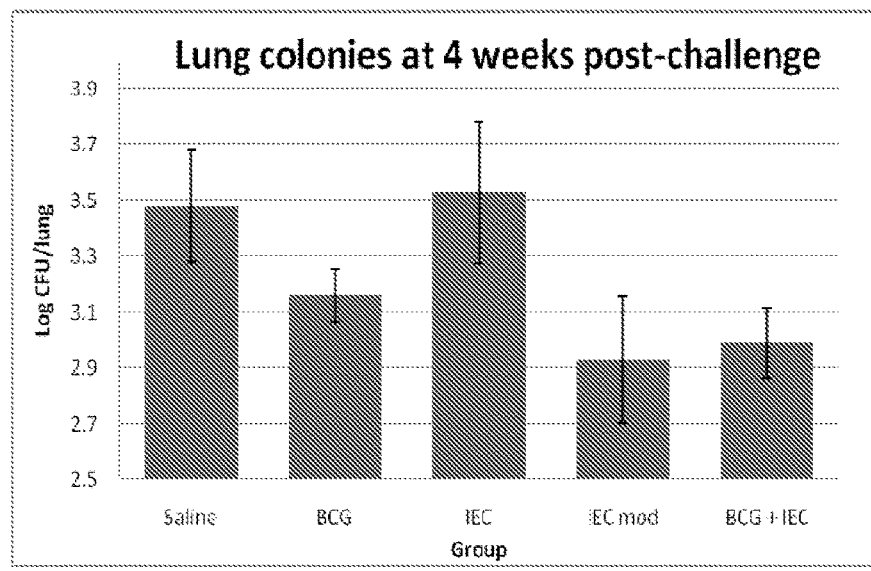
FIG. 7A shows the reduction of lung colony counts in HEP-immunised animals challenged with live TB. Animals were immunised with saline as a negative control, live BCG bacteria (BCG), HEPs isolated from BCG bacterial cell lysates either in the absence (IEC) or presence of ADP+a divalent cation (IEC), or primed with live BGC and boosted with HEPs isolated by the improved method of the invention (BCG+IEC).
FIG. 7B shows the reduction of lung colony counts in animals immunised or boosted with HEPs and challenged with live TB. Animals were immunised with saline as a negative control, live BCG vaccine (BCG), HEPs isolated from BCG bacterial cell lysates in presence of ADP plus divalent cation (V1), divalent cation alone (V3) or divalent cation plus ATP to disrupt the HspC complex (V2), or primed with BCG and boosted with the HEP vaccine (BCG+V1).
Figure 7:
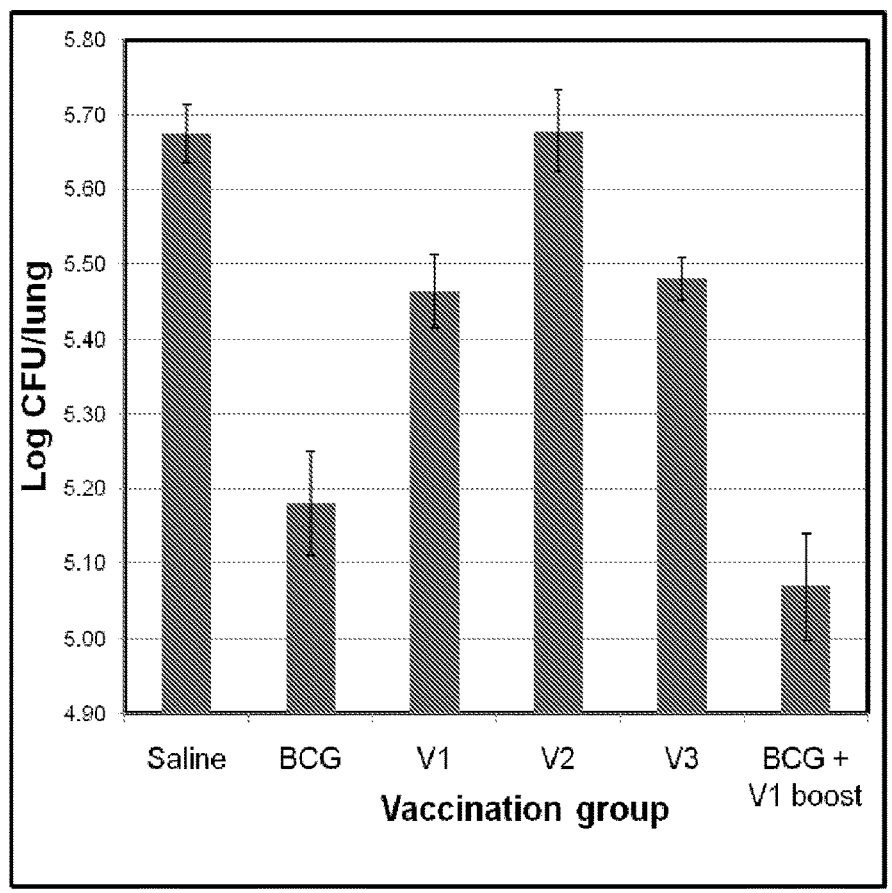

HEPs isolated from BCG as in Examples 1 (IEC) and 2 (IEC mod) were used to immunise groups of 8-10 naïve or live BCG-primed BalbC mice. Control animals were immunised with either saline or live BCG vaccine (Statens Serum Institute). HspC vaccines were dosed at 75 µg with an interval of 4 weeks between prime and booster vaccinations and 4 weeks after the final immunisations the animals were challenged with 50-100 CFU of live TB strain H37Rv. Lungs were harvested from the immunised animals 28 days after challenge and lung homogenates plated in triplicates to quantitate lung colonisation by TB. FIG. 7 shows typical CFU recovered from the lungs 4 weeks post-challenge. Animals immunised with HEPs purified using the improved buffer compositions of the present invention show significantly enhanced protection as assessed by reduced lung Cfu on live challenge (FIG. 7A. IEC mod versus IEC) and also boosted the protection induced by the current live BCG vaccine (FIG. 7A. BCG versus BCG and IEC). HEP vaccines prepared using the HspCs isolated as in Example 2 in the presence of ADP and a divalent cation (IEC mod) showed a significant protection as assayed by a reduction in lung colony counts, even better than the protection afforded by the live BCG vaccine (BCG). Boosting of animals immunised with live BCG with HspC vaccines (BCG and IEC) showed a significantly improved protection compared to those receiving BCG alone (BCG) as assessed by a further reduction in lung colony counts after H37Rv challenge.

To demonstrate the absolute requirement for the stabilisation of the HspC complexes for the enhanced protective immunogenicity seen, HEPs isolated using the improved buffer compositions of the present invention were compared to HEPs isolated in the presence of ATP to disrupt the HspC complexes. The results obtained are shown in FIG. 7B and show significant protection in animals immunised with HEPs isolated in the presence of a divalent cation (V3) and ADP (V1) compared to those purified in the presence of ATP to disrupt the HspC complexes (V2). The results also show the boosting of animals primed with the current BCG live vaccine (BCG) immunised with HEP vaccines (BCG and V1).

Example 5: Preparation of HEPs from Neisseria

Figure 3:
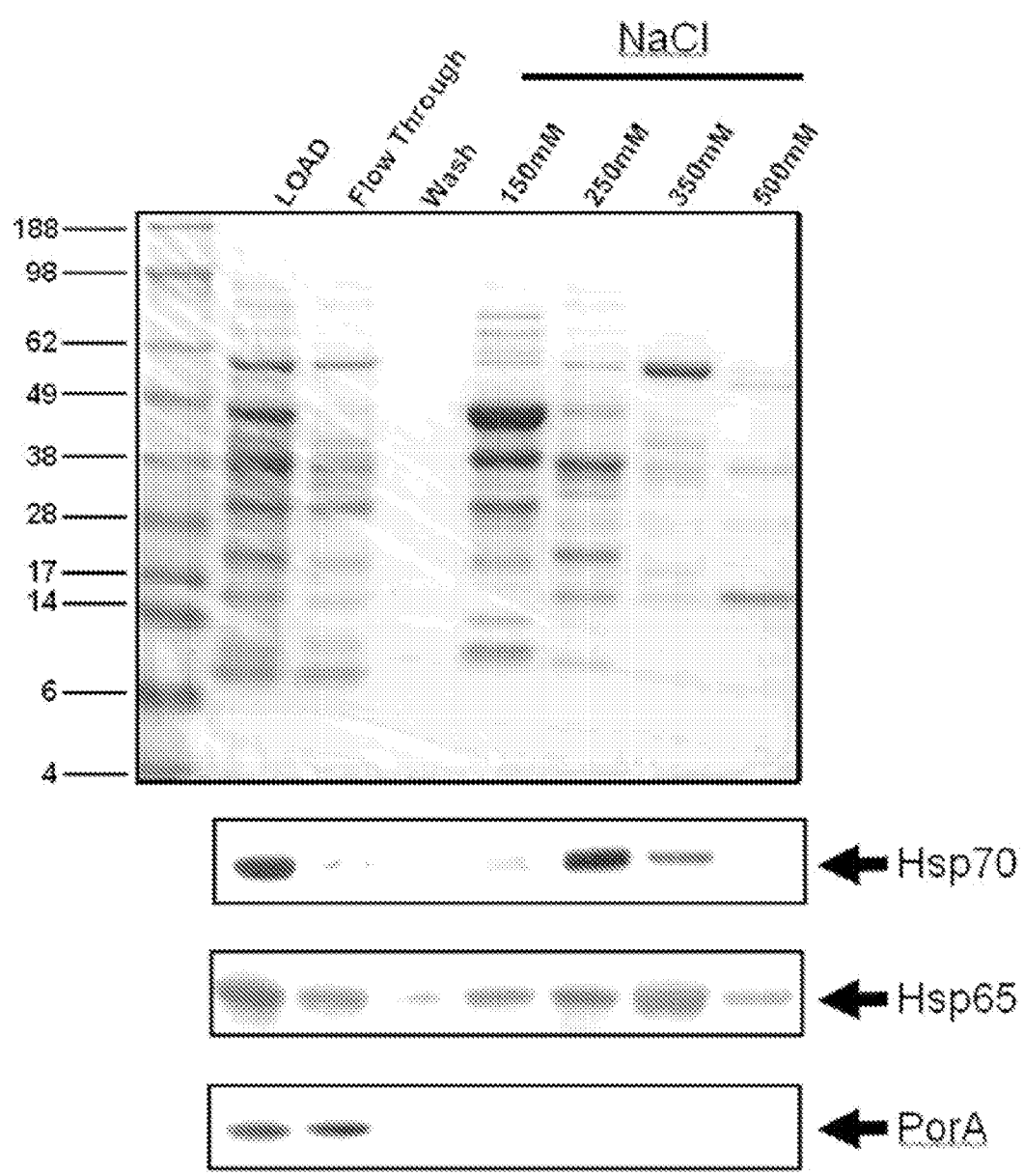
FIG. 3 shows SDS-PAGE analysis of the purification of protein complexes from *Neisseria meningitidis*, eluted by a step salt gradient and the analysis of these samples for the Hsp70, Hsp65 and PorA proteins by Western blotting.

Cultures of an acapsulate variant of Neisseria meningitidis strain MC58 (Mol Microbiol. 1995, November; 18(4): 741-54) were heat shocked at 44° C. and killed by treatment with the antibiotic gentamicin. Cells were processed to produce HEPs as described in Examples 1 and 2. In brief, cells were lysed by cycles of freezing and thawing or sonication and clarified by centrifugation for 20 minutes at 6,000 g. Clarified extract was loaded onto a column packed with CaptoQ ion exchange resin. After extensive washing of the column with 50 mM phosphate buffer, pH 6.8 proteins were batch eluted using increasing concentrations of NaCl (150 mM, 350 mM, 500 mM). Eluted fractions containing Hsp70 and Hsp65 were analysed using SDS-PAGE (FIG. 3A). Fractions eluted by 150 mM and 350 mM NaCl were combined and dialysed into PBS. Vaccine was assessed by gel electrophoresis and Western blotting for the presence of the major hsp families and the outer membrane porin, PorA. Results are shown in FIG. 3B.

Figure 8:
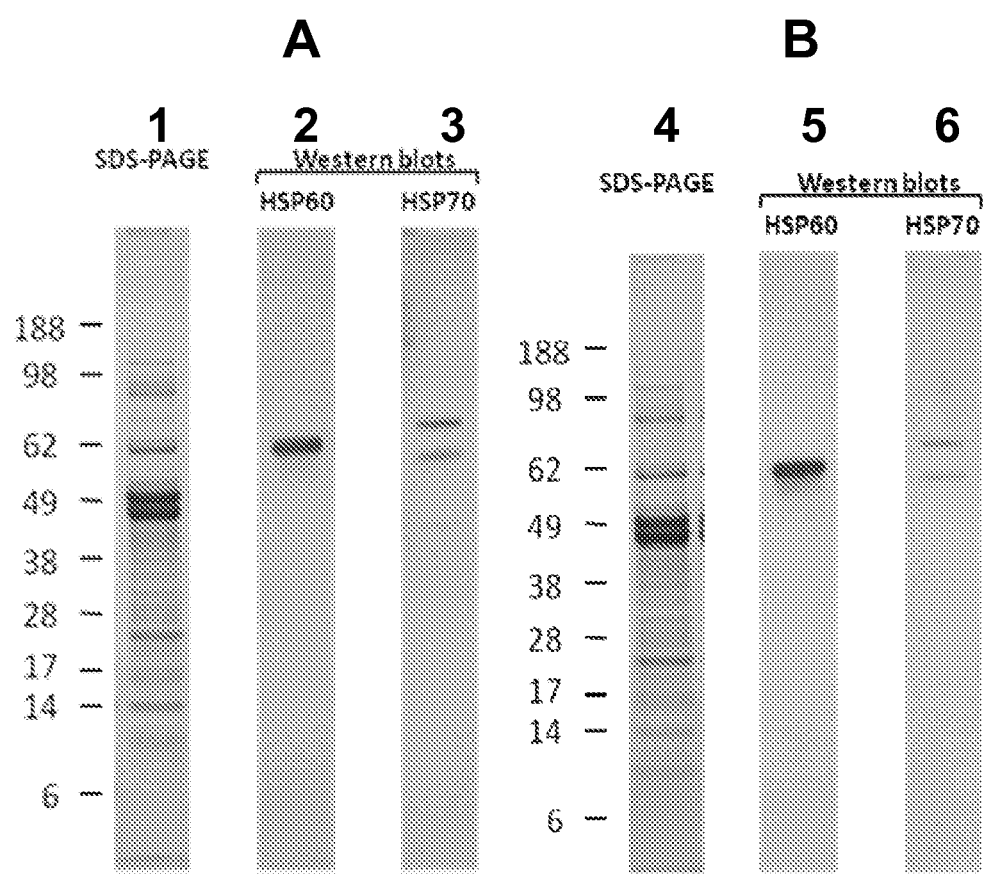
FIG. 8 shows Coomassie Blue stained SDS-PAGE (lanes 1, 4) and Western blot analysis of Hsp60 and Hsp70 in HEPs purified from *Neisseria meningitidis* either in the absence (lanes 1 to 3) or presence (lanes 4 to 6) of ADP and a divalent cation.

FIG. 8 shows HEPs from Neisseria meningitidis strain MC58 purified in the absence of ADP and a divalent cation (A) according to the method in Example 1, and in the presence of ADP and a divalent cation (B) according to the method in Example 2, and western blotted for the presence of GroEL (hsp60) and DnaK (hsp70).

Example 6: Immunogenicity of Neisserial HEPs

Figure 4:
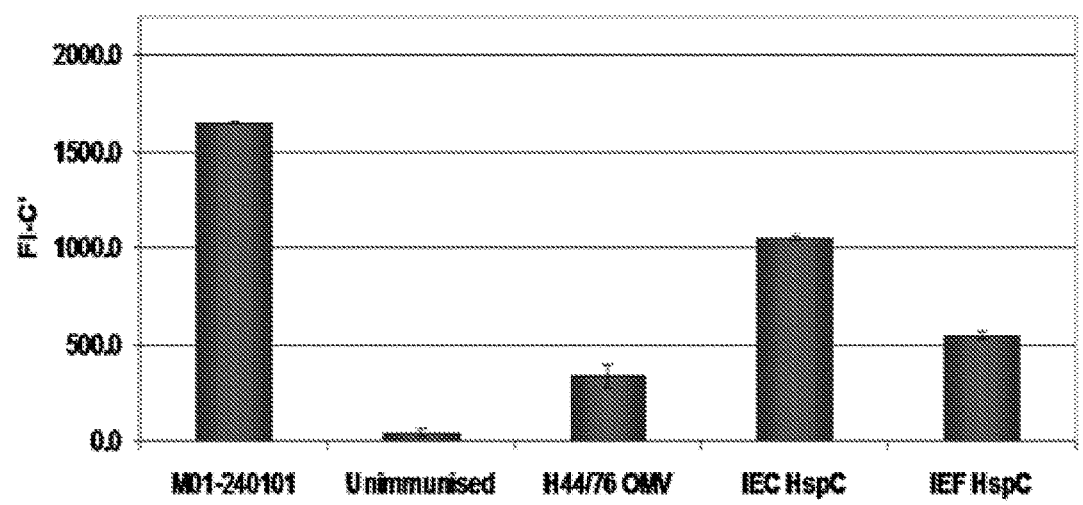
FIG. 4 shows the immunogenicity of the HEPs isolated from *Neisseria meningitidis* using the isoelectric chromatography based purification method of the present invention (IEC HspC) compared to the HEPs isolated from *Neisseria meningitidis* using conventional isoelectric focussing methods (IEF HspC). Though both HspCs showed significantly better opsonisation activity against heterologous strains than the current outer membrane vesicle vaccine (H44/76 OMV), the IEC HspCs showed better cross-strain immunogenicity than the IEF HspCs.

The HEPs prepared from Neisseria meningitidis strain MC58 or Neisseria lactamica according to the method of Example 3 were used to immunise mice in order to generate sera for assessment of cross strain responses. Sera from immunised animals were pooled and assessed for their ability to elicit cross-strain antibody-mediated opsonophagocytosis using the following clinical Neisserial strains; MC58, H44/76-SL, M01-240101, M01-240013, M01-240149, M01-240185 and M01-240355. For assay, serum samples were incubated with killed-fluorescence-labelled bacteria and IgG-depleted baby rabbit complement for 7.5 min at 37° C. HL60 cells differentiated with 0.8% DMF, were added and samples incubated for 7.5 min before the addition of ice cold DPBS to stop the reaction. Samples were analysed by flow cytometry and data expressed as a fluorescence index value (FI–C'). For all strains, serum obtained from mice vaccinated with the MC58-derived HEPs induced opsonisation responses significantly greater than those obtained with serum from non-vaccinated controls and animals immunised with hspCs purified using conventional isoelectric focussing methods or with a commercial outer membrane vesicle (H44/76 OMV) vaccine candidate. The results obtained with the heterologous strain M01-240101 are shown in FIG. 4 and show the cross-strain protection obtained with the HEPs (IEC HspC), conventionally purified hspCs (IEF HspC) and the OMV vaccine (H44/76 OMV). The HEPs vaccine also generated higher opsonisation values than the IEF HspC vaccine against both MC58 and the H44/76 strain from which the OMV vaccine was derived. HEPs isolated from a commensal Neisseria, N. lactamica using the methods in Examples 1 and 2 showed significant cross-serotype protection of mice in a lethal challenge study, with complete survival of all mice against peritoneal injection of live MC58.

Example 7: Purification and Immunogenicity of HEPs from Streptococcus pneumoniae Streptococcus pneumonia strain D39 was grown in Hoeprich's medium, heat shocked at 42° C. for 45 minutes and heat-killed at 56° C. for 15 minutes. Cells were harvested by centrifugation, resuspended in 50 mM HEPES, 1 mM MgCl$_2$, 1 mM ADP pH 6.8 and disrupted in an Emulsiflex C5. The lysate was clarified by centrifugation and loaded on a CaptoQ column and eluted in lysis buffer containing 300 mM NaCl. The purified HEPs were used to immunize BalbC mice and the sera analysed for antibodies against the various S. pneumoniae strains by ELISA. The HEPs vaccines induced good antibodies against the immunization strain D39 and cross reaction with strains 23F and TIGR4. The humoral response induced further showed a Th1 lymphocyte cell bias with the production of IgG2a subtype antibodies being greater than the production of IgG1 subtype antibodies.

Example 8: Purification and Immunogenicity of HEPs from Baculovirus Infected Insect Cells Recombinant baculovirus expressing influenza H3 Panama haemagluttinin and hepatitis C virus E1 and E2 polypeptides as fusion proteins with a human IgG Fc fragment were used to infected Sf9 insect cells. Infected cells were grown for 72 hours in Insect-Xpress protein-free media and cells pelleted at 4,500 rpm for 10 minutes in a Jouan GR422 centrifuge. Cell pellets were resuspended and lysed on ice in 10 mM Tris-HCl, pH 6.8 containing 0.2% NP40, 1 mg/ml pepstatin and 0.2 mM PMSF using a dounce homogenizer. The lysate was centrifuged at 12,000 g for 15 minutes and the supernatant centrifuged at 100,000 g for 30 minutes to yield a clarified lysate which was then loaded onto a CaptoQ™ column. The column was washed in 10 mM Tris-HCl, pH 6.8 containing 100 mM NaCl and the HEPs eluted with a 150-350 mM NaCl salt gradient. The purified HEPs were used to immunise mice and rabbits and sera from the immunized animals assayed by Western blotting and inhibition of hemagglutination.

Example 9: Purification and Immunogenicity of HEPs from Tumour Cells

EL4 and A20 cells were grown in RPMI media, lysed in buffers containing non-ionic using a Potter homogeniser and tumour cell HEPs purified and tested for immunogenicity by Western blotting as in Example 6.

Figure 9:
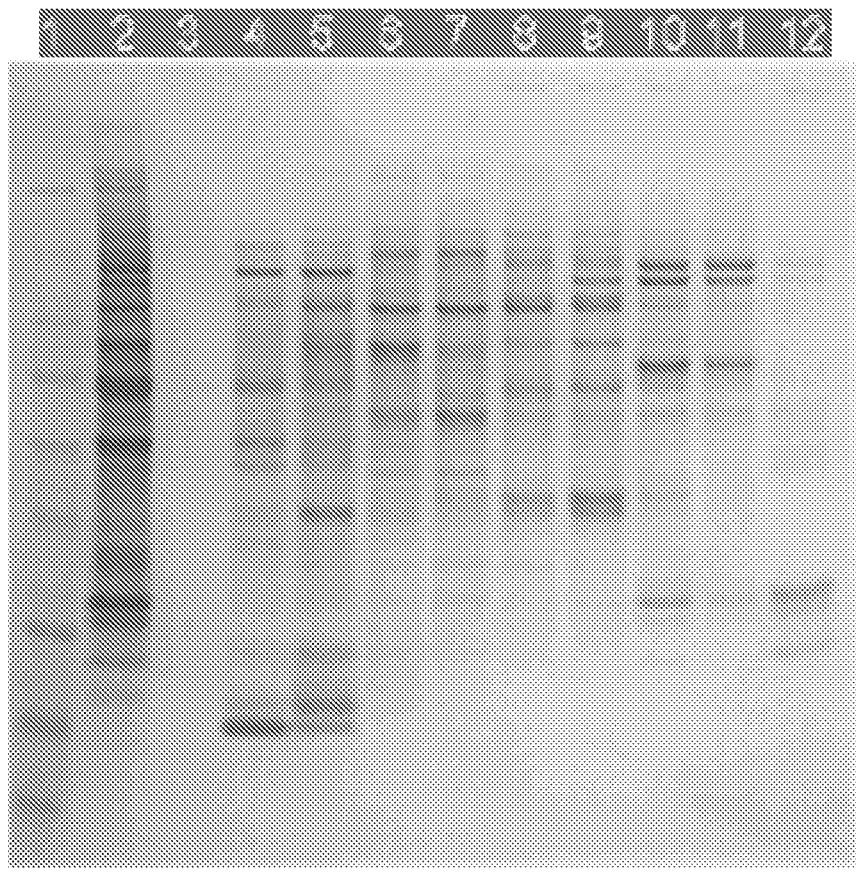
FIG. 9 shows Coomasie Blue stained SDS-PAGE analysis of the purification of HEPs from CHO cells, eluted by a step salt gradient (A) and the analysis of these samples for the Hsp70 (B) and Hsp60 (C) proteins by Western blotting. Lane 1: Mw markers, lane 2: flow through, lane 3: wash, lane 4: 150 mM elution, lane 5:150 mM elution, lane 6: 250 mM elution, lane 7: 250 mM elution, lane 8: 350 mM elution, lane 9: 350 mM, lane 10: 500 mM elution, lane 11: 500 mM elution, lane 12: 1 M elution.
Figure 9:
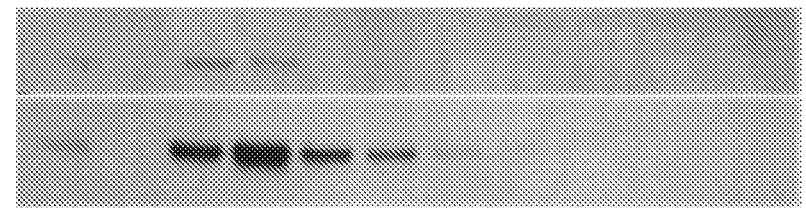

Example 10: Purification and Immunogenicity of HEPs from CHO Cells Expressing Heterologous Antigens CHO cells and CHO cells expressing Fc-fusion proteins were grown in CHO CD media (Gibco). CHO cells were harvested, washed in PBS, resuspended in 50 mM HEPES, 150 mM NaCl pH6.8 either with or without 1 mM ADP and 1 mM MgCl and lysed by sonication. The lysate was clarified by centrifugation followed by filtration through 0.8 μM and then 0.2 μM filters, diluted 10× in 50 mM HEPES pH6.8 and the HEPs purified using an AKTA chromatography system on a 1 ml CaptoQ column. The column was washed with 20 ml buffer containing 50 mM HEPES pH6.8 and B, 50 mM HEPES, 20 mM NaCl pH6.8 either with or without added 1 mM ADP and 1 mM MgCl and the HEPs eluted in wash buffer containing increasing salt concentration of 150 mM NaCl, 250 mM NaCl, 350 mM and 500 mM NaCl. HEPs were run on SDS-PAGE gels and either stained for protein with Coomassie (FIG. 9A) or Western blotted for either hsp60 (antibody SPA-875, Stressgene) or Hsp70 (antibody SPA-811, Stressgene) (FIGS. 9B and 9C respectively). The Coomassie staining demonstrates the captured proteins by CaptoQ resin from the CHO lysate and good separation of these proteins by step gradient elution. The Western blots demonstrate the elution of the HEPs from the CaptoQ column with 150 mM NaCl.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention. Reference to any prior art in this specification is not, and should not be taken as, an acknowledgment or any form of suggestion that this prior art forms part of the common general knowledge in any country.

The invention claimed is:

1. A method for the purification of target stress protein complexes with enhanced immunogenicity, formed between a plurality of stress proteins of different stress protein classes and polypeptides, the method comprising the steps of:
   (i) providing a source mixture comprising the target stress protein complexes;
   (ii) determining the isoelectric point (pI) of the target stress protein complexes;
   (iii) preparing a cell lysate from the source mixture comprising the target stress protein complexes;
   (iv) clarifying the cell lysate by subjecting the cell lysate to centrifugation and/or filtration to provide a clarified cell lysate;
   (v) transferring the clarified cell lysate of step (iv) to an ion exchange column wherein the transferred clarified cell lysate comprises all of the stress protein complexes found within the cell lysate of step (iii);
   (vi) subjecting the clarified cell lysate of step (v) to purification using ion exchange to purify the target stress protein complexes comprising the plurality of stress proteins of different protein classes and the polypeptides;
   (vii) buffering the clarified cell lysate with a primary buffer comprising at least one divalent cation to a pH within 2 units of the pI of the target stress protein complexes during ion exchange;
   (viii) providing a secondary buffer providing a salt gradient; and
   (ix) eluting the target stress protein complexes comprising the plurality of stress proteins of different stress protein classes, wherein the target stress protein complexes purified in the presence of the at least one divalent cation have enhanced immunogenicity over target stress protein complexes purified in the absence of the at least one divalent cation.

2. The method as claimed in claim 1 wherein the primary buffer of step (vii) further comprises adenosine diphosphate.

3. The method as claimed in claim 2 wherein the adenosine diphosphate is provided at a concentration of from 0.1 mM to 100 mM, and wherein the at least one divalent cation is provided at a concentration of 0.1 mM to 100 mM.

4. The method as claimed in claim 1 wherein the at least one divalent cation is a magnesium salt and/or a manganese salt.

5. The method as claimed in claim 1 wherein the primary buffer lacks at least one of adenosine triphosphate (ATP), ATPase and/or potassium or a potassium salt.

6. The method as claimed in claim 1 wherein the primary buffer does not include chaotropes, surfactants, urea or ampholytes.

7. The method as claimed in claim 1 wherein the pH of the secondary buffer is pH 6.8.

8. The method as claimed in claim 1 wherein the ion exchange is selected from the group consisting of ion exchange chromatography and mixed mode chromatography.

9. The method as claimed in claim 1 wherein the target stress protein complexes are eluted in a fraction which comprises complexes with a pI of 4.5 to 6.5.

10. The method as claimed in claim 1 wherein the target stress protein complexes are derived from the group consisting of a cancerous cell, a pathogenic cell, a cell infected by a pathogenic organism, a cell which has been genetically modified such that it expresses a heterologous protein which is derived from a cancerous cell and a cell which has been genetically modified such that it expresses a heterologous protein derived from a pathogen which causes an infectious disease in a host.

11. The method as claimed in claim 1 wherein the polypeptide of the target stress protein complexes are derived from a pathogenic organism which typically causes an infectious disease, wherein the pathogenic organism is selected from the group consisting of a prokaryotic cell, a protozoa, a virus, a parasite and a fungi or wherein the polypeptide of the at least one target stress protein is a tumour specific antigen.

12. The method as claimed in claim 8 wherein the ion exchange chromatography is selected from cation exchange chromatography and anion exchange chromatography.

* * * * *